United States Patent
LoPachin et al.

(10) Patent No.: US 8,835,510 B2
(45) Date of Patent: Sep. 16, 2014

(54) METHODS AND COMPOSITIONS FOR TREATING CONDITIONS MEDIATED BY OXIDATIVE STRESS OR ELECTROPHILIC ENVIRONMENTAL TOXINS

(75) Inventors: Richard M. LoPachin, New Rochelle, NY (US); Terrence Gavin, New Paltz, NY (US)

(73) Assignee: Montefiore Medical Center, Bronx, NY (US)

( * ) Notice: Subject to any disclaimer, the term of this patent is extended or adjusted under 35 U.S.C. 154(b) by 0 days.

(21) Appl. No.: 13/699,314

(22) PCT Filed: Jun. 1, 2011

(86) PCT No.: PCT/US2011/038670
§ 371 (c)(1),
(2), (4) Date: Jan. 25, 2013

(87) PCT Pub. No.: WO2011/156181
PCT Pub. Date: Dec. 15, 2011

(65) Prior Publication Data
US 2013/0116337 A1    May 9, 2013

Related U.S. Application Data

(60) Provisional application No. 61/397,213, filed on Jun. 8, 2010.

(51) Int. Cl.
| | | |
|---|---|---|
| *A61K 31/12* | (2006.01) | |
| *A61K 31/40* | (2006.01) | |
| *A61K 31/44* | (2006.01) | |
| *A61K 31/121* | (2006.01) | |
| *A61K 31/35* | (2006.01) | |
| *A61K 31/122* | (2006.01) | |
| *A61K 31/4015* | (2006.01) | |
| *A61K 31/341* | (2006.01) | |
| *A61K 31/357* | (2006.01) | |
| *A61K 31/055* | (2006.01) | |

(52) U.S. Cl.
CPC .............. *A61K 31/121* (2013.01); *A61K 31/35* (2013.01); *A61K 31/122* (2013.01); *A61K 31/4015* (2013.01); *A61K 31/341* (2013.01); *A61K 31/357* (2013.01); *A61K 31/055* (2013.01)
USPC .......................................................... 514/690

(58) Field of Classification Search
CPC ....... A61K 31/11; A01N 35/04; A01N 25/16; A01N 31/04; A01N 35/02
USPC .......................................................... 514/690
See application file for complete search history.

(56) References Cited

U.S. PATENT DOCUMENTS 5,152,983 A * 10/1992 Nambudiry et al. ............ 424/60
5,288,750 A *  2/1994 Pohto et al. .................... 514/438
5,441,727 A *  8/1995 Chatterjee et al. ............. 424/65

OTHER PUBLICATIONS

MedscapeNat Clin Pract Oncol CME © 2008 Nature.*
Humana Mar. 12, 2012.*
Singletary et al. (Carcinogenesis vol. 19(6) 1039-1043 (1998).*
Mayo Clinic (2004) Health Library.*
PCT International Search Report dated Oct. 24, 2011 in connection with PCT International Patent Application No. PCT/US2011/038670, 5 pages.
PCT Written Opinion of the International Searching Authority dated Oct. 24, 2011 in connection with PCT International Patent Application No. PCT/US2011/038670, 5 pages.
Aggarwal B B et al., entitled "Molecular Targets and Therapuetic Uses of Curcumin in Health and Disease," New York: Springer, 2007, ISBN-13:978-0-387-46-400-8; pp. 77-125 and 343-357.

* cited by examiner

*Primary Examiner* — Shirley V Gembeh
(74) *Attorney, Agent, or Firm* — Amster, Rothstein & Ebenstein LLP

(57) ABSTRACT

Methods and compositions are disclosed for treating a subject with a disease or tissue injury mediated by cellular oxidative stress or with an environmental toxicity due to an electrophilic toxicant or pollutant, and for providing a nutritional supplement to a subject and for providing a skin treatment for a subject, where the methods comprise administering to the subject a 1,3-dicarbonyl compound.

15 Claims, 7 Drawing Sheets

AcAc

TFPD

Dimedone

A. Curcumin structure

B. Keto-enol equilibration

C. Enolate formation

METHODS AND COMPOSITIONS FOR TREATING CONDITIONS MEDIATED BY OXIDATIVE STRESS OR ELECTROPHILIC ENVIRONMENTAL TOXINS

CROSS-REFERENCE TO RELATED APPLICATIONS

This application is a U.S. national stage entry under 35 U.S.C. §371 of PCT International Patent Application No. PCT/US2011/038670, filed Jun. 1, 2011, which claims priority to U.S. Provisional Patent Application No. 61/397,213, filed Jun. 8, 2010, the contents of which are incorporated herein by reference in their entirety.

STATEMENT OF GOVERNMENT SUPPORT

This invention was made with government support under grant number RO1 ES03830 21-24 awarded by the National Institute of Environmental Health Sciences. The government has certain rights in the invention.

BACKGROUND OF THE INVENTION

Throughout this application various publications are referred to in superscript. Full citations for these references may be found at the end of the specification. The disclosures of these publications are hereby incorporated by reference in their entirety into the subject application to more fully describe the art to which the subject invention pertains.

It is now recognized that many environmental toxicants (e.g., acrolein, chlorpyrifos methyl-mercury), as well as the endogenous mediators of cellular oxidative stress (e.g., free radicals, metal ions, unsaturated aldehydes), are electron deficient species (i.e., electrophiles). Substantial evidence indicates that these electrophilic toxicants cause cell damage by reacting with nucleophilic targets on biological macromolecules[21, 37, 53, 55, 58, 59, 60, 62, 73, 83, 84]. Thus, for example, α,β-unsaturated carbonyl/aldehyde compounds (type-2 alkenes) are an important class of environmental pollutants that includes acrolein, acrylamide and methyl vinyl ketone. Humans are pervasively exposed to these chemicals through natural sources, diet, industrial pollution and occupation, and the toxicological consequences of such exposures have been well documented[14, 45, 58, 94]. The common α,β-unsaturated carbonyl/aldehyde structure of the type-2 alkenes is a soft electrophile, and current evidence suggests that these chemicals cause toxicity by forming 1,4-Michael adducts with the soft nucleophilic thiolate state of protein sulfhydryl groups[17, 22, 45, 56, 57, 61, 77].

Electrophilic species also play a prominent role in cellular oxidative stress, which is defined as an imbalance between the production of reactive oxygen species (ROS) and their removal via endogenous antioxidant systems. Oxidative stress is not only involved in the normal aging process, but is a pathogenic feature of many diseases (e.g., atherosclerosis, diabetes, Alzheimer's disease) and tissue injury states (e.g., spinal cord trauma, stroke). It is initiated by univalent reduction of molecular oxygen to form the superoxide anion radical. Subsequent dismutation via superoxide dismutase (SOD) yields hydrogen peroxide, which is converted via the metal ion (Cu, Fe)-catalyzed Fenton reaction to the highly toxic hydroxyl radical. This electron-deficient species can damage cells by direct interactions with macromolecules (e.g., DNA/RNA base oxidation, oxidative protein damage) and through membrane lipid peroxidation. Peroxidative fragmentation of polyunsaturated fatty acids (e.g., arachidonic and linoleic acids) generates lipid hydroperoxides that can undergo chain cleavage to yield toxic α,β-unsaturated aldehyde derivatives such as acrolein and 4-hydroxy-2-nonenal (HNE; reviewed in[33, 42, 49, 59, 61, 81]). These endogenous derivatives are highly reactive electrophiles that readily form adducts with nucleophilic sidechains on protein cysteines and other amino acid residues (e.g., see[56, 52, 62]; reviewed in[28, 77, 94]). Such protein adduct formation has been linked to broad cytotoxic consequences including inhibition of enzyme activity, mitochondrial dysfunction and disruption of cell signaling pathways. Accordingly, the "aldehyde burden" imposed by lipid peroxidation is now thought to be a critical pathogenic component of cellular oxidative stress[5, 39, 69, 95, 96, 97] (reviewed in[18, 27, 58, 60].) Oxidative stress can, therefore, be viewed as the sequential generation of electrophiles that mediate cell injury and death. Thus, electrophiles are a large class of endogenous and exogenous toxicants that play significant roles in pathophysiological processes.

Pharmacological treatment (e.g., N-acetyl cysteine) of many environmentally-derived toxicities (e.g., acrylamide contaminated well-water or industrial acrylonitrile poisoning) has often met with limited success. Moreover, many of the current pharmacotherapeutic venues (e.g., antioxidant therapy—α-tocopherol, β-carotene) available for treatment of certain disease states (e.g., Parkinson's disease) and traumatic injuries (e.g., spinal cord injury) are either palliative or have disappointing effectiveness. The complexity of the underlying etiologies is the likely explanation for the limited performance of these therapies. The research community almost uniformly agrees that the effective management of these pathogenic states will require either, a therapeutic "cocktail" involving several drugs or a multifunctional compound that can block the pathophysiological cascade at multiple rate-limiting steps. The present invention addresses the need for improved methods and compositions for treating subjects with diseases and tissue injury conditions that have cellular oxidative stress as a molecular etiology, such as atherosclerosis, diabetes, Alzheimer's disease, stroke and traumatic spinal cord injury, and for treating subjects with environmentally-derived toxicities.

SUMMARY OF THE INVENTION

The present invention provides methods of treating a subject with a disease or tissue injury mediated by cellular oxidative stress or a subject with an environmental toxicity due to an electrophilic toxicant or pollutant, the methods comprising administering to the subject a therapeutically effective amount of a compound of formula (I) as described herein.

The invention also provides methods of providing a nutritional supplement to a subject comprising administering to the subject a compound of formula (I) as described herein.

The invention further provides methods of treating the skin of a subject comprising administering to the skin of the subject a compound of formula (I) as described herein.

The invention further provides compositions i) for treating a subject with a disease or tissue injury mediated by cellular oxidative stress, ii) for treating a subject with an environmental toxicity due to an electrophilic toxicant or pollutant, iii) for treating a subject's skin, and iv) as nutritional supplements, the composition comprising a compound of formula (I) as described herein.

DETAILED DESCRIPTION OF THE INVENTION

Figure 1:
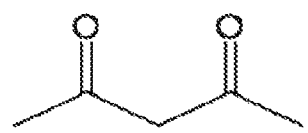
FIG. 1. Structures of acetylacetone (AcAc), 1,1,1-trifluoropentanedione (TFPD), and 5,5-Dimethyl-1,3-cyclohexanedione (Dimedone).
Figure 1:
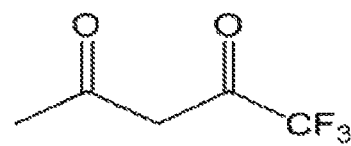
Figure 1:
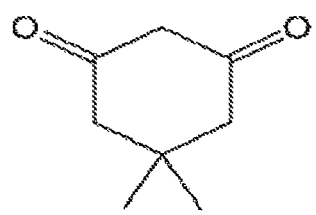

The present invention provide a method of treating a subject with a disease or tissue injury mediated by cellular oxidative stress or a subject with an environmental toxicity due to an electrophilic toxicant or pollutant, the method comprising administering to the subject a therapeutically effective amount of a compound of formula (I)

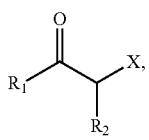

(I)

wherein $R_1$ and $R_2$ are independently H, alkyl, alkoxy alkyl, acyloxy alkyl, aryl, aryloxy, acyloxy aryl, heteroaryl, heteroaryloxy, or acyloxy heteroaryl; X is $COR_3$, $CO_2R_3$, $NO_2$, CN, $CON(R_3)_2$, or $SO_2R_3$; $R_3$ is H, alkyl, alkoxy alkyl, acyloxy alkyl, aryl, aryloxy, acyloxy aryl, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —CH3, —NH2, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

As used herein, to treat a subject with a disease or tissue injury mediated by cellular oxidative stress or a subject with an environmental toxicity due to an electrophilic toxicant or pollutant means to alleviate a sign or symptom associated with the disease, injury or environmental toxicity.

The disease or tissue injury can be, for example, atherosclerosis, diabetes, Alzheimer's disease, stroke or traumatic spinal cord injury.

The environmental electrophilic toxicant or pollutant can be, for example, acrolein, acrylamide, methyl vinyl ketone, chlorpyrifos methyl-mercury, an α,β-unsaturated aldehyde derivative, an α,β-unsaturated carbonyl derivative, a heavy metal, an organophosphate insecticide, acrylamide contaminated well-water or an industrial acrylonitrile. For example, the subject can have mercury (Hg), lead (Pb) or arsenic (As) poisoning. An electrophile is attracted to electrons and participates in a chemical reaction by accepting an electron pair in order to bond to a nucleophile. A nucleophile forms a chemical bond to its reaction partner (the electrophile) by donating both bonding electrons.

The compounds can be used, for example, to prevent or reduce hepatotoxicity.

The invention also provides a method of providing a nutritional supplement to a subject comprising administering to the subject a compound of formula (I)

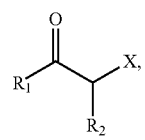

(I)

wherein $R_1$ and $R_2$ are independently H, alkyl, alkoxy alkyl, acyloxy alkyl, aryl, aryloxy, acyloxy aryl, heteroaryl, heteroaryloxy, or acyloxy heteroaryl; X is $COR_3$, $CO_2R_3$, $NO_2$, CN, $CON(R_3)_2$, or $SO_2R_3$; $R_3$ is H, alkyl, alkoxy alkyl, acyloxy alkyl, aryl, aryloxy, acyloxy aryl, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —CH3, —NH2, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

The invention further provides a method of treating the skin of a subject comprising administering to the skin of the subject a compound of formula (I)

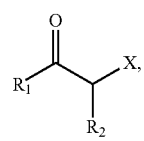

(I)

wherein $R_1$ and $R_2$ are independently H, alkyl, alkoxy alkyl, acyloxy alkyl, aryl, aryloxy, acyloxy aryl, heteroaryl, heteroaryloxy, or acyloxy heteroaryl; X is $COR_3$, $CO_2R_3$, $NO_2$, CN, $CON(R_3)_2$, or $SO_2R_3$; $R_3$ is H, alkyl, alkoxy alkyl, acyloxy alkyl, aryl, aryloxy, acyloxy aryl, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —CH3, —NH2, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

The compound can be used, for example, to prevent or treat an aging effect on the skin or to prevent or treat sun damage to the skin. For example, the compound can be used to treat or prevent wrinkles.

The invention further provides a composition i) for treating a subject with a disease or tissue injury mediated by cellular oxidative stress, ii) for treating a subject with an environmental toxicity due to an electrophilic toxicant or pollutant, iii) for treating a subject's skin, or iv) for providing a nutritional supplement to a subject, the composition comprising a compound of formula (I)

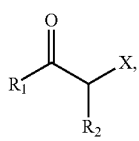
(I)

wherein $R_1$ and $R_2$ are independently H, alkyl, alkoxy alkyl, acyloxy alkyl, aryl, aryloxy, acyloxy aryl, heteroaryl, heteroaryloxy, or acyloxy heteroaryl; X is $COR_3$, $CO_2R_3$, $NO_2$, CN, $CON(R_3)_2$, or $SO_2R_3$; $R_3$ is H, alkyl, alkoxy alkyl, acyloxy alkyl, aryl, aryloxy, acyloxy aryl, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group; wherein any alkyl can independently be branched or unbranched; wherein any aryl or heteroaryl can independently be optionally substituted with —CH3, —NH2, —OH, =O, halogen, alkyl, alkoxy, acyloxy, aryl and/or acyloxyaryl; or a tautomer thereof; or a geometric or optical isomer thereof; or racemate thereof; or a pharmaceutically acceptable salt thereof.

The compound used in the any of the methods disclosed herein or in any of the compositions disclosed herein can have, for example, the structure

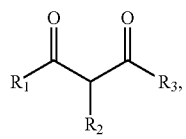

or that of its enol tautomers

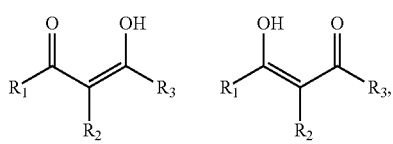

or any anionic species formed from either the dione or enols with the following structure

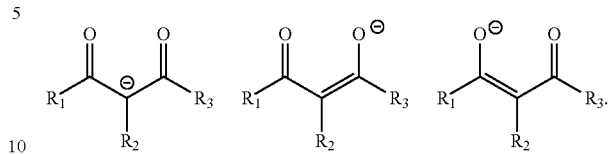

In any of the compounds used in any of the methods disclosed herein or in any of the compositions disclosed herein, any ring formed between $R_2$ with $R_1$ and/or $R_3$ can be independently a 4-12 member ring, for example, a 5-6 member ring. Furthermore, any ring formed between $R_2$ with $R_1$ and/or $R_3$ can independently contain one or more O, S, N or substituted N, where substitution at N is any alkyl or acyl group.

In any of the compounds used in any of the methods disclosed herein or in any of the compositions disclosed herein, any alkyl can be independently C1-C6 alkyl, for example, C1-C3 alkyl.

The compound used in the any of the methods disclosed herein or in any of the compositions disclosed herein can also have, for example, the structure

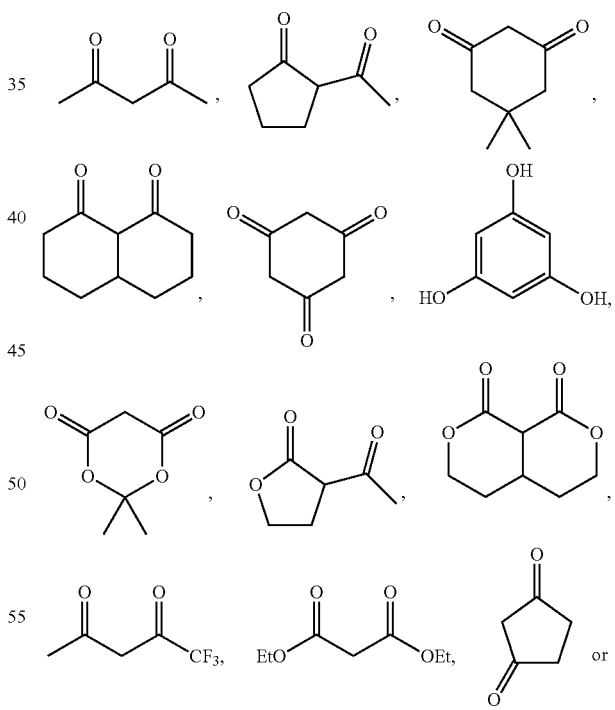

wherein $R_4$=H, alkyl, alkoxy, acyloxy, aryl or acyloxyaryl; or a tautomer thereof.

More preferred compounds include

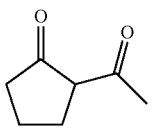

or a tautomer thereof.

Pharmaceutically acceptable salts that can be used include non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The compounds can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intranasal administration, and administration through an osmotic mini-pump.

The compounds can be applied to the skin, for example, in compositions formulated as skin creams, or as sustained release formulations or patches.

The invention also provides for the use of a compound of formula (I) for treating a subject with a disease or tissue injury mediated by cellular oxidative stress or with an environmental toxicity due to an electrophilic toxicant or pollutant. The invention further provides for the use of a compound of formula (I) as a nutritional supplement or for treating the skin.

Compounds that can be used in the methods of the present invention can be obtained commercially from, e.g., Sigma-Aldrich Inc., or prepared using methods well known to those familiar with the art of organic synthesis.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Figure 2A:
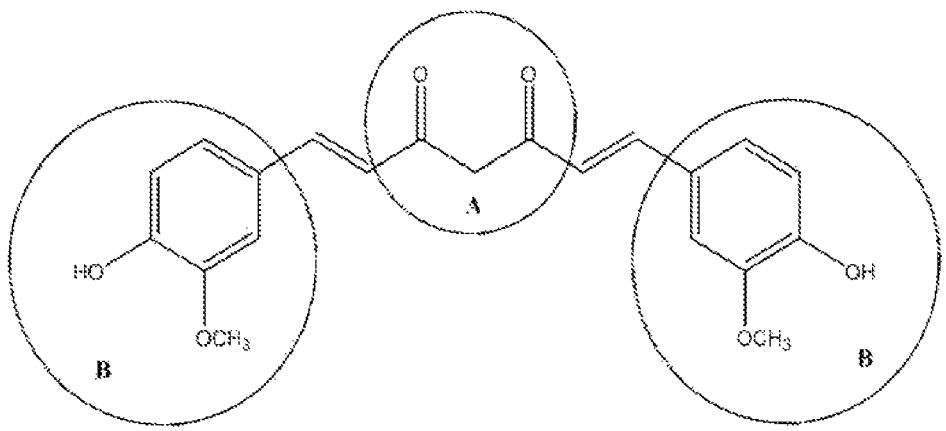
FIG. 2A-2C. A) Curcumin is a hydrophobic multifunctional compound. It consists of a 1,3-dione system (circled "A"), two phenol portions (circled "B") and two carbon-carbon double bonds (not circled), which are conjugated with both the aromatic systems and the carbonyl functions. Curcumin exists as an equilibrating pair of keto-enol isomers (shown in B), rather than the circled ("A") diketo structure shown in A). The phenol groups of curcumin (circled "B") have generated significant attention based on their presumed role in antioxidant behavior. However, recent evidence indicates that the antioxidant properties of this phytopolyphenol are due to the effects of "A" and "B". Thus, in ionizing solutions, deprotonation of enol (shown in C) yields the highly nucleophilic enolate carbanion, which can trap electrophilic free radicals.

Enolates formed from 1,3-dicarbonyl compounds, such as acetylacetone (AcAc) and dimedone (DMD), are highly nucleophilic carbanions that can readily react with or scavenge electrophiles (FIG. 1). Because electrophiles (e.g., acrolein, metal cations, oxygen radicals) are key components of many pathogenic scenarios (e.g., heavy metal poisoning, oxidative stress), it was hypothesized that AcAc and other 1,3-dicarbonyls might provide significant cytoprotection through their ability to scavenge toxic electrophiles. Indeed, as demonstrated herein, a series of 1,3-dicarbonyl derivatives provided cytoprotection in several experimental models of electrophile toxicity (see below). Although the idea that 1,3-dicarbonyl compounds might be cytoprotective is unprecedented, it is based on the recognition that curcumin, phloretin and other plant-derived polyphenolic compounds (phytopolyphenols) also exhibit ionizable enol moieties that appear to be responsible for their well-documented antioxidant and antiinflammatory properties (FIG. 2A). However, certain chemical characteristics of these polyphenolic chemicals, which the non-phenolic 1,3-dicarbonyls do not possess, could limit clinical utility, i.e., chemical instability, toxicity and poor bioavailability. Thus, 1,3-dicarbonyl enol compounds represent a rational basis for designing safe, efficacious cytoprotectants with broad therapeutic applications.

Curcumin, Phloretin and Related Phytopolyphenols: Enolate-Based Cytoprotection.

Figure 2B:
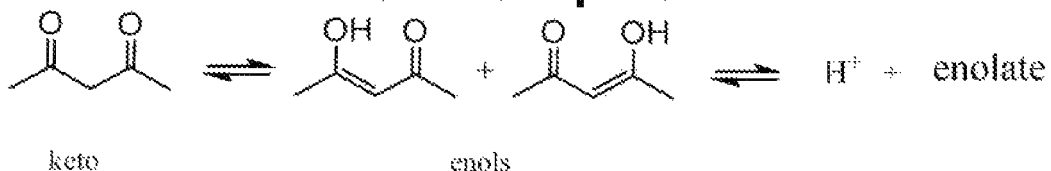
Figure 2C:
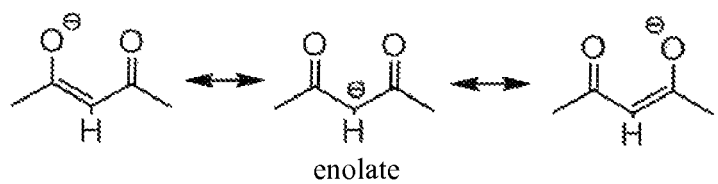

There is abundant evidence that plant-derived polyphenolic compounds (phytopolyphenols) have cytoprotective properties with broad clinical applications. For example, curcumin (*Curcuma longa* Linn) is the active ingredient in numerous traditional medicines of China and India (FIG. 2A)[3, 35]. Research has shown that curcumin has antioxidative, anti-inflammatory, chemopreventive and antitumor properties (reviewed in[35, 67, 79]). Corresponding clinical trials have demonstrated that this phytopolyphenol is useful in treating numerous diseases; e.g., Alzheimer's disease, epilepsy, cervical cancer and diabetes (reviewed in[3, 35, 38]). Human consumption of other naturally occurring polyphenols, such as the flavonoids (e.g., resveratrol in red wine, phloretin in apple skins and epigallocatechin gallate in green tea), has been associated with a reduction in the incidence of cancer, stroke and coronary heart disease (reviewed in[6, 15, 44, 64, 99]). Basic research has shown that the flavonols, chalcones and other dietary flavonoids have significant cytoprotective actions in various in vitro systems and animal models (e.g., see[19, 26, 36]). Until recently, it was assumed that the protective effects of these compounds were related to their antioxidant actions. However, evidence now indicates that cytoprotection is more complex and involves not only free radical trapping, but also metal ion chelation and scavenging of toxic aldehyde species; e.g., acrolein and HNE (4-hydroxy-2-nonenal). The structural determinant of these cytoprotective effects is the enol moiety of the phytopolyphenol structure. In this regard, the central heptadienone bridge of curcumin (circled A of FIG. 2A) is considered to be critical[12, 89, 93]. This moiety exists as equilibrating keto-enol isomers with the enol form predominating in ionizing solutions such as biological buffers (FIG. 2B). The enol of curcumin is a 1,3-dicarbonyl; i.e., two carbonyl groups separated by one (α) carbon. The hydrogens at the central α-carbon of such enol compounds are acidic and, when removed, a carbanion is formed as the conjugate-base. The resulting anionic enolate, like most bases, is a site of nucleophilic reactivity (FIG. 2C). Similarly, flavonoid polyphenols (e.g., phloretin) are characterized by multiple dicarbonyl enol moieties (note: all phenols are enols). Phloretin, for example, has at least three enolic sites that can potentially form a highly nucleophilic enolate anion (structures not shown).

Relation of Enolate Nucleophilicity to Phytopolyphenol Cytoprotection:

Electrophiles such as free radicals, metal ions and aldehyde by-products are important pathogenic components of oxidative stress. Therefore, nucleophile-based scavenging of these toxic electrophiles has substantial cytoprotective potential. Evidence provided by Litwinienko and Ingold[50] indicated that the nucleophilic enolate of curcumin initially reacts with free radicals to form a β-diketonyl radical. This is followed by proton donation from the phenol and, through a process known as single proton loss electron transfer (SPLET), an electron migrates through the delocalized system to restore the keto-enol group and convert the phenolate to a phenoxyl radical. Flavonoid polyphenols also quench free radicals via a similar mechanism of enolate-trapping and proton donation[70, 100]. The nucleophilic enolate moiety of curcumin also functions as a bidentate chelator of iron [Fe(III)], copper [Cu(II)] and other electrophilic metal ions[10, 43, 88]. The chelation chemistry of curcumin is based on the well-described process of Fe(III) chelation by the nucleophilic enolate of AcAc. Flavonoids also chelate metals through a curcumin-like mechanism[64, 65, 70]. Metal ion chelation presumably affords cytoprotection by limiting the participation of iron and copper in the Fenton reaction and thereby reducing subsequent generation of the highly toxic hydroxyl radical. Finally, several classes of flavonoids including the flavan-3-ols, theaflavins and dihydrochalcones were shown to form adducts with acrolein, HNE and other electrophilic α,β-unsaturated carbonyl/aldehyde products of lipid peroxidation[13, 51, 72, 80, 85, 101, 102]. Phloretin was the most effective flavonoids tested and mass spectrometric analyses showed that electrophile adduction was mediated through the C-3 enol site[85, 102]. A growing body of evidence[2, 40, 46, 78] also suggests that curcumin can scavenge acrolein and HNE through the enolate moiety. As will be discussed, the ability to adduct toxic aldehydes has substantial mechanistic relevance to cytoprotection. Thus, curcumin and the flavonoid compounds have multiple cytoprotective actions likely linked to the nucleophilicity of enolate moieties. The pleiotropic character of phytopolyphenols has tremendous implications for efficacious cytoprotection, since the oxidative stress cascade could be truncated at numerous steps; i.e., the Fenton reaction, subsequent free radical dissemination and toxic aldehyde generation.

Phytopolyphenol Disadvantages:

Despite numerous potentially beneficial actions, there are significant disadvantages that might ultimately limit the clinical applications of phytopolyphenols. Wang et al.[92] reported that curcumin in phosphate buffer (pH 7.2, 37 C) was 90% decomposed within 30 minutes. These investigators identified a primary decomposition product, trans-6-(4'-hydroxy-3'-methoxyphenyl)-2,4-dioxo-5-hexenal, and several minor products; e.g., vanillin, ferulic acid and feruloylmethane. The observation that these decomposition products (e.g., ferulic acid) were also associated with in vivo administration suggested that curcumin is unstable in physiological solutions. There is also growing in vitro evidence that curcumin and certain flavonoids are cytotoxic, primarily through ROS-mediated cell damage; e.g., see[31, 32, 47, 71, 82, 87, 98]. Perhaps more problematic, the phytopolyphenols exhibit limited bioavailability[15, 75], which is likely related to the water insolubility of the polyphenolic structure. The limited bioavailability poses numerous pharmaceutical and formulary issues (e.g., large doses, lipidated formulations) that must be addressed if the phytopolyphenols are to be used clinically.

1,3-Dicarbonyl Enols: A New Class of Cytoprotectants:

As discussed above, the cytoprotective properties of phytopolyphenols appear to be related to the nucleophilic enolate of the corresponding enol moieties. The central heptadienone bridge of curcumin, which has been identified as the seat of corresponding cytoprotective actions, is a 1,3-dicarbonyl enol (FIG. 2A). AcAc, MPD and structurally related derivatives are non-phenolic 1,3-dicarbonyl chemicals (FIG. 1). Like curcumin, these chemicals exist as keto-enol tautomers with the enol isomer predominating in biological solutions. Ionization yields the highly nucleophilic anionic enolate[63]. The shared nucleophilic enolate moiety suggests that the 1,3-dicarbonyl compounds exhibit a cytoprotection profile similar to that of curcumin. Indeed, metal ion chelation is a well-documented trait of the 1,3-dicarbonyl compounds[63, 87] and, although not as well studied, free radical trapping is a potential property[50]. The 1,3-dicarbonyls also exhibit the phytopolyphenolic property of aldehyde adduction; i.e., AcAc and several analogs formed adducts with soft electrophilic chemicals (i.e., benzhydrylium ions[16]). In several in vitro models of aldehyde (acrolein) toxicity, many of the same 1,3-dicarbonyl enols were highly cytoprotective through formation of 1,4-Michael adducts. This presumption has significant precedence since Michael addition, one of the most well known reactions in organic chemistry, was originally defined by the conjugate addition of an enolate ion to an αβ-unsaturated aldehyde derivative[63]. Thus, the 1,3-dicarbonyls compounds and the dietary polyphenols can undergo common chemical reactions (i.e., metal chelation, free radical trapping and aldehyde adduction) that have broad cytoprotective implications. However, in contrast to the phytopolyphenols, the 1,3-dicarbonyls (FIG. 1) are simple, non-phenolic and can be relatively water-soluble compounds. Aqueous-solubility suggests that the bioavailability of these compounds is greater than that of curcumin and other dietary polyphenols. The 1,3-dicarbonyls enols are also chemically stable compounds with limited toxicity at the cellular (FIG. 4) and whole animal (AcAc $LD_{50}$=175 mg/kg) levels. Finally, quantum mechanical calculations ($\omega^-$, Table 1; see also[11]) indicate that the nucleophilic reactivity of AcAc and related analogs is significantly higher than that of the curcumin enolate. This suggests that the cytoprotective efficacy of the 1,3-dicarbonyl compounds could be substantial.

Example I

Chemistry of the 1,3-Dicarbonyl Protectants and Cytoprotection Studies

Chemistry of the 1,3-Dicarbonyl Protectants

The invention relates to the therapeutic and medicinal use of compounds with the general formula (I):

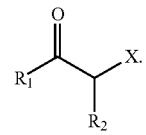

Quantum Mechanical Calculations of Enolate Nucleophilicity:

The Hard and Soft, Acids and Bases (HSAB) theory of Pearson[58, 62, 76] is a predictive chemical model based on the premise that soft electrophiles preferentially react with soft nucleophiles and hard electrophiles react with hard nucleophiles. This is a quantifiable concept where the designation of "hard" or "soft" is based on corresponding inherent electronic characteristics that can be computed from the energies of the respective frontier molecular orbitals; i.e., the Highest Occupied Molecular Orbital ($E_{HOMO}$) for the nucleophile or the Lowest Unoccupied Molecular Orbital ($E_{LUMO}$) for the electrophile. These energies have been used to develop valid quantum mechanical parameters that define the electrophilicity ($\omega$) and nucleophilicity ($\omega^-$)[41] of chemical species. Application of these parameters has significantly increased understanding of electrophile and nucleophile behavior in various biological systems[56, 57, 61, 68]. Accordingly, the $\omega^-$ algorithm was used to calculate the relative nucleophilicities of several 1,3-dicarbonyl compounds and curcumin using acrolein as the electrophilic target (Table 1). Computations of nucleophilicity included the keto and enol isomers and the anionic enolate. Because the $\omega^-$ values for the enol and keto isomers of all chemicals considered were substantially lower (100 fold) than the respective enolate values (data not shown), it can be concluded that the enolate form is the relevant nucleophile; i.e., acrolein reacts the enolate, rather than with the enol or keto isomers. When other electrophile targets were applied (e.g., methylvinyl ketone, benzhydrylium ions) in the $\omega^-$ algorithm, the same enolate reactivity was evident (data not shown). Finally, it is noteworthy that the curcumin enolate is significantly less nucleophilic than the enolate forms of the 1,3-dicarbonyl compounds (Table 1).

TABLE 1

Nucleophilicities and kinetic data for 1,3-dicarbonyl enol compounds.

| Enolate | $\omega^-$ | pKa |
| --- | --- | --- |
| DEM | 0.228 | 12.9 |
| MPD | 0.230 | 10.8 |
| ACP | 0.401 | 7.8 |
| DMD | 0.174 | 5.3 |
| AcAc | 0.169 | 9.0 |
| Meld. Acid | 0.166 | 4.8 |
| TFPD | 0.099 | 4.7 |
| phloretin | 0.105 | 7.3 |
| curcumin | 0.062 | 8.0 |

The $E_{LUMO}$ and $E_{HOMO}$ energies were calculated using Spartan08 (version 1.0.3) software (Wavefunction Inc., Irvine Calif.). The nucleophilicity index ($\omega^-$) was calculated as $\omega^- = \eta_A(\mu_A-\mu_B)^2/2(\eta_A-\eta_B)^2$, where A=the selected enol and B=acrolein. Global (whole molecule) softness ($\sigma$) was calculated as the inverse of hardness or $\sigma=1/\eta$, where hardness ($\eta$)=($E_{LUMO}-E_{HOMO}$)/2 and $\mu=(E_{LUMO}+E_{HOMO})/2$. All values are presented as electron volts (see LoPachin et al.[56, 57] for details). Abbreviations: DEM=diethyl malonate; MPD=3-methyl-2,4-pentanedione; ACP=2-acetylcyclopentanone; DMD=dimedone; AcAc=acetylacetone; Meldrum's acid=2,2-dimethyl-1,3-dioxane-4,6-dione; TFPD=1,1,1,-trifluoro-2,4-pentanedione.

Cytoprotection Studies:

The idea that 1,3-dicarbonyl compounds are cytoprotective was completely unexplored and, therefore, a series of studies was conducted to determine respective in vitro cytoprotective capacities. To determine the predictive value of $\omega^-$ calculations, respective nucleophilicities (Table 1) were calculated for the 1,3-dicarbonyl enol compounds and were compared to the corresponding kinetic data. Kinetic assays show that the rate of sulfhydryl loss associated with acrolein incubation was slowed predictably by a structural series of enols. Furthermore, this kinetic order predicted the relative abilities of enol analogs to prevent acrolein-induced toxicity in complex biological models, i.e., isolated striatal synaptosomes (nerve endings) and a cultured nerve cell line.

Figures 3A, 3B:
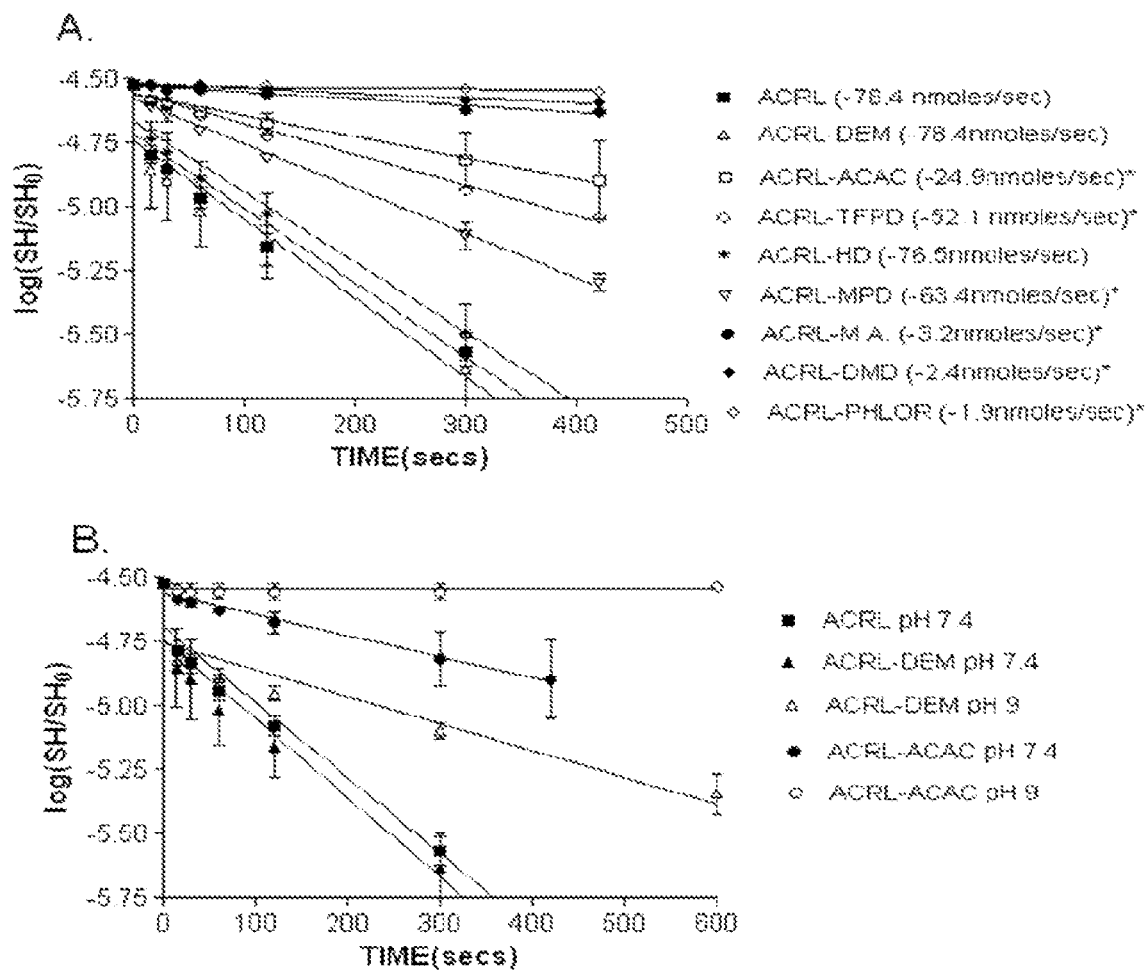
FIG. 3A-3B. A) Relative abilities of dicarbonyl analogues in vitro to slow N-acetyl cysteine (NAC) sulfhydryl loss induced by acrolein co-incubation. The slope of each regression line represents the pseudo-first order rate constant, which is presented parenthetically. B) shows the effect of elevated pH on sulfhydryl protection provided by AcAc or DEM.

1,3-Dicarbonyl Protection of Sulfhydryl Groups: Kinetic Analyses and Synaptosome Model:

As an index of cytoprotection, these studies focused on the abilities of 1,3-dicarbonyl compounds to prevent electrophile-induced loss of protein and non-protein sulfhydryl groups. This experimental focus is based on substantial evidence that soft electrophiles, like acrolein, produce toxicity by forming Michael-type adducts with soft nucleophilic thiolate (anionic sulfhydryl) groups on functionally critical proteins[9, 17, 22, 56, 57] (reviewed in[28, 58, 62, 77, 94]). If the nucleophilic enolates of 1,3-dicarbonyl derivatives are cytoprotective through scavenging electrophiles, then these enols should be capable of slowing the adduct reaction between an electrophile and a corresponding nucleophilic target. To test this hypothesis, a determination was made of the ability of AcAc and other structurally related enol analogs to prevent sulfhydryl (nucleophile) adduction by acrolein (electrophile)[56]. In this study, N-acetyl cysteine (NAC) was used as a sulfhydryl source and was incubated with both acrolein (150 µM) and a selected test compound (50 µM) in Krebs buffer (pH 7.4, 30° C.). Free sulfhydryl concentrations were determined over time (up to 15 mins) by the DTNB method of LoPachin et al.[52]. The adduct reaction between acrolein and NAC (FIG. 3A) followed pseudo-first order kinetics[56, 57] as indicated by the linear relationship ($r^2$ range=0.82-0.99) between log [SH/SH$_O$] versus time (where SH=sulfhydryl concentration at time t and SH$_O$=initial concentration at t$_O$). Results indicate that the 1,3-dicarbonyl derivatives acted as surrogate nucleophilic targets and thereby slowed the loss of NAC sulfhydryl groups due to acrolein adduction (FIG. 3A). Specifically, acrolein alone caused a rapid reduction (mean rate±SE) in sulfhydryl concentration (rate=−78.4±7 nmol SH sec$^{-1}$). However, when acrolein was co-incubated with DMD or phloretin, the rate of sulfhydryl loss was substantially curtailed (−2.4±0.3 and −1.9±0.7 nmol SH sec$^{-1}$, respectively). AcAc (−24.9±5 nmol SH sec$^{-1}$) was somewhat less protective, whereas TFPD afforded modest, roughly equivalent, reductions in thiol loss (−52.1±5 nmol SH sec$^{-1}$). MPD was minimally protective (FIG. 3A), whereas DEM and 2,5-hexanedione (HD), a γ-diketone (i.e., carbonyl functions separated by two carbon atoms), were not effective at slowing the rate of thiol loss (FIG. 3A). To demonstrate that the formation of the enolate was dependent upon enol ionization, the thiol protection afforded by DEM, AcAc and TFPD was determined at pH 9.0 (FIG. 3B). AcAc (pKa 9.0—Table 1) at pH 9.0 was completely protective, whereas the ability of DEM (pKa 12.9—Table 1) to slow acrolein-induced thiol loss was significantly increased. This pH-dependent effects reflects the increased enolate concentration at pH 9.0, which is closer to the pKa of AcAc and DEM. In contrast, the protective capacity of TFPD did not increase at the more basic pH (data not shown), since at neutral pH this 1,3-dicarbonyl analog is mostly (99%) in the enolate-state (pKa 4.7—Table 1).

Figure 4:
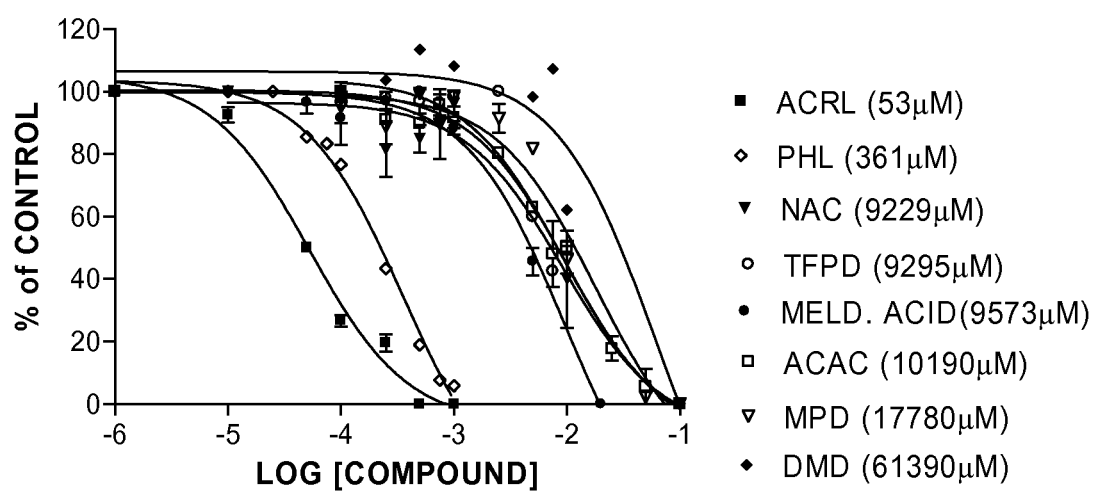
FIG. 4. Effects of 1,3-dicarbonyl compounds and phloretin (PHL), a phytopolyphenol, on radiolabeled dopamine (DA) membrane transport in control striatal synaptosomes. Results demonstrate the weak toxicity of the 1,3-dicarbonyl analogs and the relatively significant in vitro toxicity of phloretin.
Figure 5A:
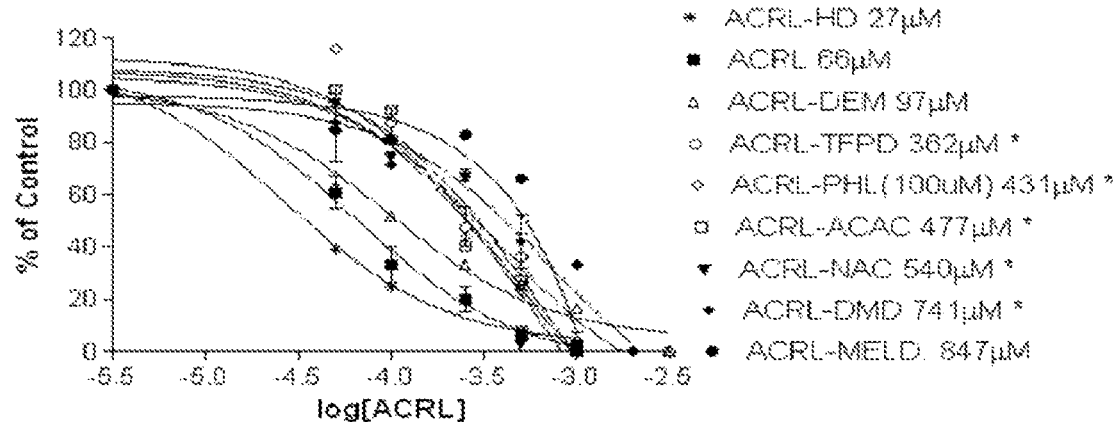
FIG. 5A-5B. Effects of 1,3-dicarbonyl or phloretin (PHL) on the inhibition of radiolabeled dopamine (DA) transport (A) and loss of free sulfhydryl groups (B) in acrolein-exposed striatal synaptosomes.

Because acrolein and other electrophilic α,β-unsaturated carbonyl derivatives produce toxicity through preferential adduction of protein sulfhydryl groups, the preservation of thiols in the preceding kinetic studies (FIG. 3) suggests that the 1,3-dicarbonyl derivatives have protective actions. Therefore, as an investigation of possible cytoprotection, a determination was made of the relative abilities of the above 1,3-dicarbonyl structural series to prevent thiol loss in acrolein-exposed rat striatal synaptosomes (isolated CNS nerve terminals). Synaptosomes were prepared according to the methods of LoPachin et al.[52] and were exposed (Krebs buffer, pH 7.4, 30° C.×15 mins) to graded concentrations of acrolein (1-1000 µM) alone or in combination with a 1,3-dicarbonyl derivative or control compound (500 μM). The 1,3-dicarbonyl concentration was selected based on initial concentration-response determinations, which showed that 500 μM provided thiol protection against an acrolein concentration that caused a 50% loss of sulfhydryl groups ($IC_{50}$; data not shown). Synaptosomal sulfhydryl content was determined by a DTNB method (see above) and data were fitted by nonlinear regression analysis ($r^2$ for all curves ≥0.90). The respective $IC_{50}$s and 95% confidence intervals were calculated by the Cheng-Prusoff equation (Prism 3.0, GraphPad Software). The selected 1,3-dicarbonyls are carbanion nucleophiles and, therefore, the analyses also included NAC as a representative thiolate-type nucleophile. Studies were conducted to assess the in vitro toxicity of the selected enol derivatives (FIG. 4). Based on the respective $IC_{50}$s, the 1,3-dicarbonyl compounds are relatively weak toxicants (i.e., mM $IC_{50}$s), whereas the phytopolyphenol, phloretin, exhibits significant synaptosomal toxicity (i.e., μM $IC_{50}$s). As shown in FIG. 5A, the enols shifted the concentration-response curve to the right for acrolein-induced inhibition of DA transport, which resulted in corresponding increases in the acrolein $IC_{50}$. Thus, DMD, Meldrum's acid, AcAc and NAC produced the largest increases in the acrolein $IC_{50}$, whereas the changes induced by TFPD were more modest (FIG. 5A). Neither DEM nor HD significantly affected the acrolein $IC_{50}$. The rank order of synaptosomal function (FIG. 5A) and thiol (FIG. 5B) protection by the enol analogs was equivalent to that defined in the preceding kinetic studies (FIG. 3A). This rank order reflects both the respective pKa values of the 1,3-dicarbonyl derivatives and corresponding nucleophilicities (Table 1). Specifically, DMD, with a pKa value of 5.3, will exist primarily (99%) as the acrolein-scavenging anionic enolate at pH 7.4. Based on the significant nucleophilicity of this analog ($\omega^-=0.174$), it is not surprising that DMD is a powerful cytoprotectant. DEM is a better nucleophile ($\omega^-=0.228$) than DMD; however, it is not cytoprotective since very little enolate (<0.1%) is available at neutral pH given a pKa of 12.9. Although TFPD is a weaker nucleophile ($\omega^-=0.099$) than the other enol analogs (Table 1), this derivative offers some thiol protection at pH 7.4 through mass action of the more abundant enolate form (pKa=4.7).

Figure 6:
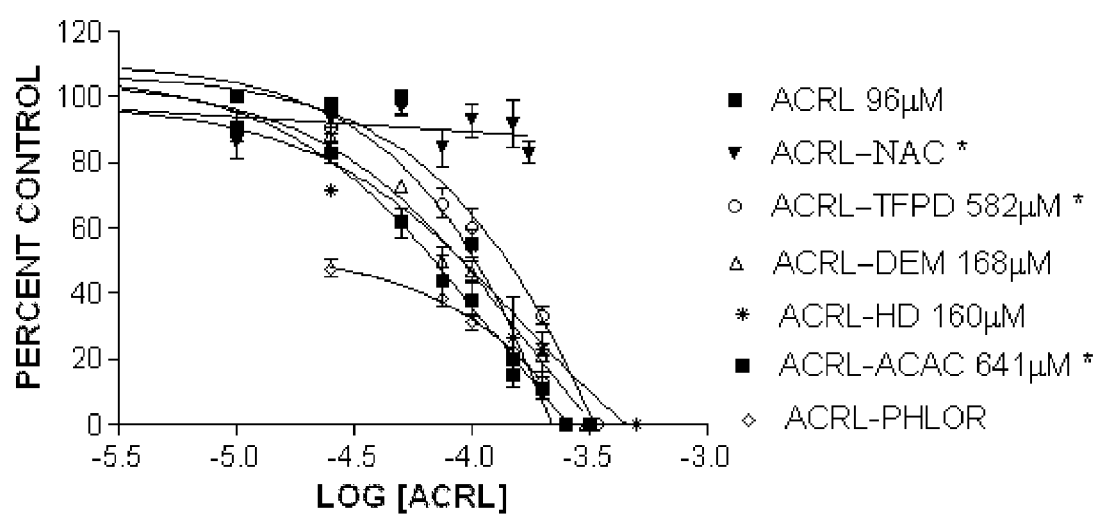
FIG. 6. Effects of 1,3-dicarbonyl derivatives or phloretin (PHLOR) on cell viability in acrolein-exposed MN9D cultures. Data are expressed as mean percentage control, and calculated $LC_{50}$s for loss of cell viability are provided.
Figure 7:
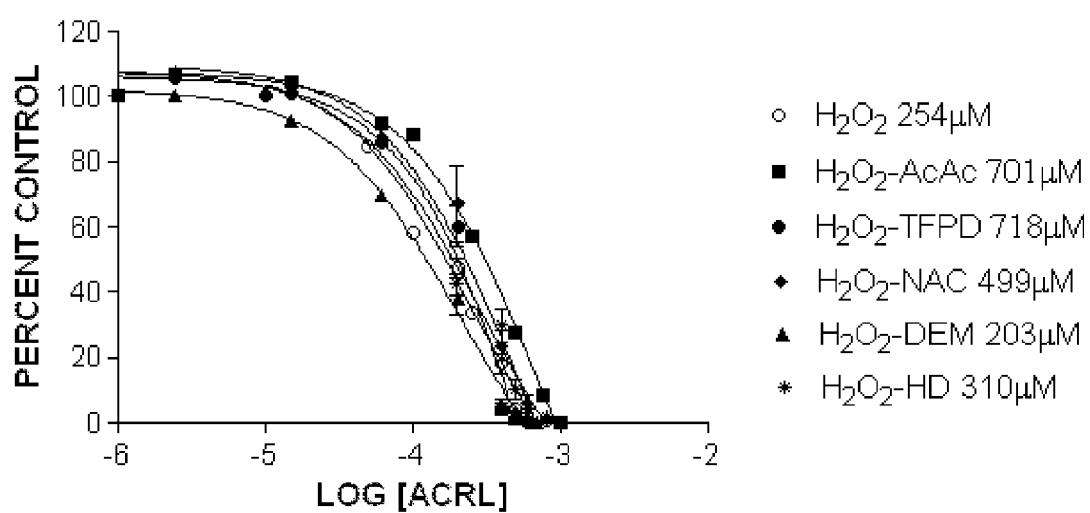
FIG. 7. Effects of 1,3-dicarbonyl on cell viability in $H_2O_2$-exposed MN9D cultures (n=3-4 experiments). Data are expressed as mean percentage control SEM, and calculated $LC_{50}$s for loss of cell viability are provided.

1,3-Dicarbonyl Protection of Sulfhydryl Groups: Nerve Cell Culture Models:

The demonstrated ability of the 1,3-dicarbonyl analogs to prevent acrolein-induced thiol loss suggests that the nucleophilic enolate of these chemicals could provide significant cytoprotection by scavenging electrophilic mediators (e.g., free radicals, toxic aldehydes and metal ions) of oxidative stress. As a more complex biological model, a determination was made of the relative abilities of the 1,3-dicarbonyls to protect MN9D cells, a dopaminergic cell line, from acrolein- (FIG. 6) or hydrogen peroxide ($H_2O_2$)-induced cell death (FIG. 7). Briefly, two days after plating, cells were incubated with AcAc (750 μM) for one hr followed by exposure to graded concentrations of either acrolein (0.50-150 μM×24 hrs) or $H_2O_2$ (50-750 μM×24 hrs). Cell viability was determined by trypan blue (0.1%) exclusion. Living cells were counted in a hemocytometer and total cells per dish were calculated. Range-finding studies showed that AcAc (50-1000 μM) provided concentration-dependent protection against both acrolein- and $H_2O_2$-induced toxicity. Exposure of cells to graded concentrations of acrolein (50-150 μM) caused cell death with an $LC_{50}$ of 96 μM ($LC_{50}$=acrolein concentration producing 50% cell lethality; FIG. 6). Preincubation with AcAc or TFPD caused rightward shifts in the respective acrolein curves and nearly 7-fold increases in the $LC_{50}$ (641 μM or 582 μM; FIG. 6). As expected, neither DEM nor HD were effective (FIG. 6). NAC provided nearly complete protection against acrolein cytotoxicity, whereas phloretin (PHLOR; 100 μM) alone caused substantial cell loss (~50%) and did not protect MN9D cell from acrolein.

The relative abilities of the 1,3-dicarbonyl compounds to protect cells against $H_2O_2$ toxicity was also determined (FIG. 7). This system represents a more complete model of oxidative stress since the hydroxyl radical formed from intracellular $H_2O_2$ during the Fenton reaction, subsequently mediates the generation of toxic aldehyde by-products such as acrolein and 4-hydroxy-2-nonenal (HNE). The data show that AcAc and TFPD provide 3-fold protection against $H_2O_2$-induced cytotoxicity. In contrast, NAC was significantly less efficacious and both DEM and HD were ineffective.

Conclusions:

Depending upon the respective pKa and nucleophilicity values, DMD, AcAc and other 1,3-dicarbonyl analogs provide substantial cytoprotection in several models of electrophile toxicity. Unlike conventional antioxidants such as alpha-tocopherol and beta-carotene that trap free radicals, the dicarbonyls have a broad profile of electrophile scavenging; e.g., hydroxyl radicals, metal ions and toxic unsaturated aldehydes. In contrast, to the phytopolyphenols (phloretin, curcumin, resveratrol), the 1,3-dicarbonyls are water-soluble, chemically stable and non-toxic. The possibility that these chemicals have significant cytoprotective properties has not been considered previously. These compounds, therefore, are outstanding candidates for pharmacotherapeutic approaches to diseases and tissue injury conditions that have cellular oxidative stress as a molecular etiology.

These highly nucleophilic (electron-rich) compounds are potentially useful in the prevention and treatment of broad pathogenic states, the etiologies of which involve electrophile (electron-deficient)-induced cell damage (cytotoxicity). These electrophiles cause cell injury and death by reacting with and thereby disabling functionally critical nucleophilic sites on biological macromolecules such as proteins and DNA. The cytotoxic electrophiles include environmental contaminants (e.g., acrolein, heavy metals, organophosphate insecticides) and endogenous mediators of cellular oxidative stress (e.g., oxygen radicals, metal cations and unsaturated aldehydes). The present invention provides a surrogate nucleophilic target for electrophiles and thereby protects cells from toxicity. The invention has substantial therapeutic application given the ubiquitous presence of electrophilic toxicants in the environment and the almost generic involvement of oxidative stress in many disease processes and tissue injury conditions; e.g., atherosclerosis, diabetes, Alzheimer's disease, stroke and traumatic spinal cord injury. Pleitropic compounds can intercept the toxic actions of electrophiles (i.e., free oxygen radicals, metal cations, unsaturated aldehydes) at multiple sites along the oxidative stress cascade. Thus, the invention is envisioned to be useful in treating chemical intoxication, since the majority of environmental toxicants are electrophiles. Therefore, these compounds and structurally related analogs could be highly efficacious pharmacotherapeutic agents that have broad applications.

Example II

In Vitro Studies with 2-Acetylcyclopentanone (2-ACP)

In vitro studies were conducted with 2-acetylcyclopentanone (2-ACP):

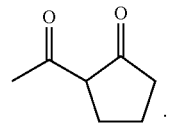

Relative to phytopolyphenols such as curcumin and resveratrol, 2-ACP is non-toxic and water soluble. As such, this 1,3-dicarbonyl derivative has substantial bioavailability and, should, therefore provide in vivo cytoprotection at relatively low doses (see Example III). Furthermore, the corresponding nucleophilic index ($\omega^-$) is relatively high (0.401 ev) (cf. Table 1) and the pKa (7.8) is close to physiological pH (7.4). This means that the anionic enolate of 2-ACP is highly nucleophilic (reflected by the $\omega^-$ value) and that at cellular pH, nearly 50% of 2-ACP will be in enolate state. This is in contrast to other putative protectants that have lower enolate nucleophilicity (e.g., curcumin) and/or higher pKa values (e.g., DEM).

Result are summarized below and described more fully in LoPachin et al. 2011,[103] the contents of which are herein incorporated by reference.

Chemicals and Reagents:

Reagents were HPLC grade, and water was double-distilled and de-ionized, unless otherwise indicated. 3H-Dopamine (specific activity 23.5 Ci/mmol) was obtained from American Radiolabeled Chemicals (St. Louis, Mo., USA). Whatman GF/F filter paper was purchased from the Brandel Company (Gaithersburg, Md., USA). MN9D cells were a gift from Lisa Won, Ph.D., University of Chicago. All other reagents were purchased from the Sigma/Aldrich Chemical Company (Bellefonte, Pa., USA). b-Dicarbonyl enols and other test compounds were dissolved in DMSO and were diluted in buffer to final concentrations of ≤0.05% DMSO. Studies showed that this DMSO concentration did not affect 3H-DA uptake or cell viability.

Figure 5B:
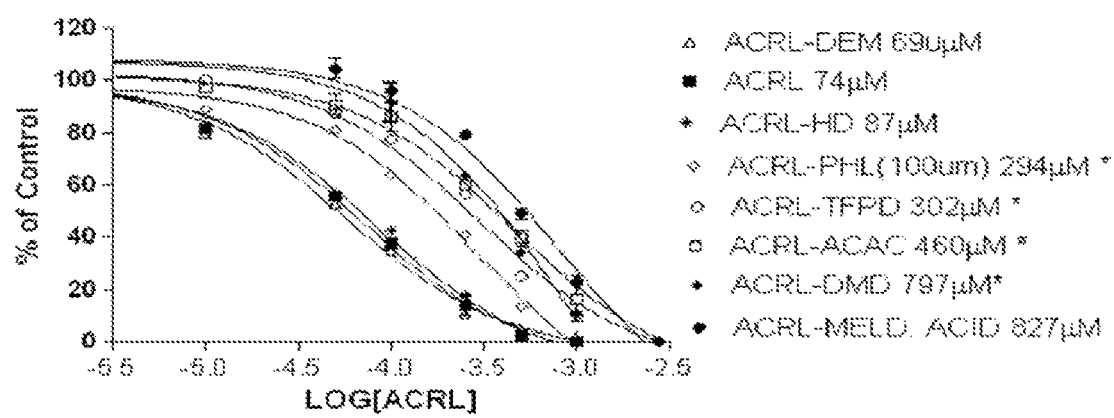

1,3-Dicarbonyl Protection Against Acrolein-Induced Synaptosomal Thiol Loss and Dysfunctional $^3$H-Dopamine (DA) Transport:

Studies were carried out using isolated brain nerve terminals (striatal synaptosomes) exposed to acrolein as a model of electrophile-induced toxicity, as illustrated in FIG. 5A-5B. Acrolein is a soft electrophile that inhibits protein function by forming adducts with soft nucleophilic cysteine residues and thereby causes synaptosomal toxicity. The ability was assessed of 2-ACP and other related 1,3-dicarbonyl analogs (500 μM) to prevent acrolein-induced inhibition of $^3$H-dopamine (DA) transport and thiol loss. Acrolein (0.001-1 mM) produced concentration-dependent loss of synaptosomal sulfhydryl groups ($IC_{50}$=74 μM), which was associated with parallel decreases in membrane $^3$H-DA transport ($IC_{50}$=66 μM). Co-incubation with 2-ACP provided substantial protection as evidenced by a rightward shift in the acrolein response curves and a 15-fold increases in the corresponding $IC_{50}$ values for both thiol preservation (1109 μM) and inhibition of $^3$H-DA transport ($IC_{50}$=947 μM). This indicates that 2-ACP was significantly more protective than other 1,3-dicarbonyl analogs or the phytopolyphenols tested; e.g., by comparison of the respective $IC_{50}$ values for 2-ACP vs., e.g., Meldrum's acid (MA) or acetylacetone (AcAc).

1,3-Dicarbonyl Protection of a Neuronal Cell Line: Acrolein and Hydrogen Peroxide Toxicities:

Pre-incubation of MN9D cell cultures for 60 minutes with 2-ACP, 1,3-cyclopentanedione (CPD) or N-acetyl cysteine (NAC) (750 μM each) completely prevented cell death induced by subsequent exposure to graded concentrations of acrolein (25-200 μM) (cf. FIGS. 6 and 7). AcAc and 1,1,1-trifluoro-2,4-pentanedione (TFPD) significantly increased the acrolein $LC_{50}$ (96 μM), whereas 2,5-hexanedione (HD) a γ-diketone analog, produced a slight increase in $LC_{50}$. Dimedone (DMD) and MA did not provide protection in acrolein-exposed MN9D cell cultures. However, this lack of cytoprotection was related to serum protein binding, since studies in serum-free medium demonstrated that both 1,3-dicarbonyl derivatives produced substantial increases in the acrolein $LC_{50}$. Studies of individual 1,3-dicarbonyls showed that graded concentrations of 2-ACP (100-750 μM) or AcAc (250-1000 μM) produced significant increases in the $LC_{50}$ reflected by progressive rightward shifts in the acrolein-induced cell death curve. Thus, the rank-order of protection from acrolein-induced toxicity in MN9D cultures mirrors that demonstrated in acrolein-exposed synaptosomes (i.e., 2-ACP≈NAC, CPD>AcAc, TFPD>>HD). Studies indicated that, although the β-dicarbonyl compounds did not cause toxicity, phloretin was a significant cytotoxicant exhibiting an $LC_{50}$ of 362 μM. Phloretin (100 μM) caused significant MN9D cell death (42%) and did not provide cytoprotection in acrolein-exposed cultures.

As a more direct model of oxidative stress, MN9D cell cultures were exposed to graded $H_2O_2$ concentrations (200-800 μM; $LC_{50}$=254 μM) and the relative abilities of dicarbonyl and polyphenolic analogs to prevent cell death were determined 2-ACP provided nearly complete protection in this injury model, whereas AcAc and TFPD were modestly effective (750 μM). Graded concentrations of 2-ACP (250-750 μM) or AcAc (500-1500 μM) produced significant increases in the $LC_{50}$ of $H_2O_2$ reflected by progressive rightward shifts in the concentration-toxicity curves. NAC was less protective and both CPD and HD were ineffective. Phloretin (100 μM) did not provide protection and instead potentiated $H_2O_2$ toxicity. Together, the results indicate that the rank-order of β-dicarbonyl protection in $H_2O_2$-exposed MN9D cell cultures was similar to those of the acrolein models; i.e., 2-ACP>AcAc, TFPD>>HD. However, there were notable exceptions: although both NAC and CPD provided protection against acrolein-induced toxicity in the synaptosomal and cell culture models, they failed to protect MN9D cells against peroxide-induced cell death.

Free Radical Scavenging:

The relative abilities of selected 1,3-dicarbonyl compounds to scavenge free radicals were determined using the spectrophotometric method of Ak and Gulcin (2008)[4] that measures changes in the absorbance of the 2,2-diphenyl-1-picrylhydrazyl radical. Consistent with previous studies, 2,2-diphenyl-1-picrylhydrazyl radical (DPPH.) scavenging by curcumin was substantially faster than any compound tested. The thiol nucleophile, N-acetyl cysteine (NAC), exhibited modest free radical scavenging, whereas phloretin and the 1,3-dicarbonyl compounds were relatively weak DPPH. scavengers; e.g., 2-ACP was approximately 30-40 fold slower than curcumin.

Metal Chelation:

The chelation of ferrous ion by a selected 1,3-dicarbonyl or other experimental compound was estimated by the method of Dairam et al. (2008).[104] Based on the concentration at which 50% $Fe^{2+}$ chelation occurs, EDTA (31 μM) and the 1,3-dicarbonyl, 2-ACP (211 μM) were the most potent chelating agents tested. AcAc was weaker (909 μM), whereas the other 1,3-dicarbonyl congeners tested, phloretin and NAC exhibited little, if any, $Fe^{2+}$ chelating activity. Consistent with previous studies, curcumin chelation of $Fe^{2+}$ paralleled that of 2-ACP up to 100 μM. Higher curcumin concentrations were not tested due to its insolubility in aqueous solutions.

Acrolein-Induced Thiol Loss:

The formation of Michael adducts with acrolein and other α,β-unsaturated aldehydes has long been considered a characteristic reaction of 1,3-dicarbonyl compounds, and it has recently been demonstrated that phloretin also forms this type of adduct with acrolein. Therefore, as a kinetic index of competitive thiol protection by enolate sequestration, the relative in vitro abilities of 1,3-dicarbonyl compounds and phloretin to slow the rate of acrolein-induced sulfhydryl loss were measured. Acrolein caused a rapid reduction (mean rate±95% confidence interval) in sulfhydryl (NAC) concentration; i.e., rate=−78.4±6.2 nmol s$^{-1}$. When acrolein was pre-incubated with 2-ACP followed by the addition of NAC one hour later, corresponding sulfhydryl groups were completely preserved. MA, DMD and phloretin provided significant thiol protection, whereas AcAc, CPD and TFPD were modestly effective. HD did not affect the rate of acrolein-induced thiol loss. When acrolein was co-incubated with the test compounds (i.e., all chemicals added simultaneously), 2-ACP again provided complete sulfhydryl protection, whereas phloretin, and the other 1,3-dicarbonyls were only marginally protective. The respective differences in protection afforded by the pre- and co-incubation conditions reflects the relative rates of reaction between acrolein and the selected 1,3-dicarbonyl analogs. Thus, 2-ACP provided complete sulfhydryl protection regardless of the incubation scenario, indicating a relatively rapid rate of acrolein interaction. In contrast, thiol protection by the other congeners required pre-incubation with acrolein indicating a significantly slower reaction rate.

To demonstrate the role that acid strength (pK$_a$) plays in the sulfhydryl protection afforded by the β-dicarbonyls, kinetic studies of thiol protection were conducted at pH 9.0. Results showed that increasing the pH substantially elevated the sulfhydryl preservation of AcAc and diethylmalonate (DEM). With pKa values of 8.9 and 12.9 respectively, the enolate concentrations of DEM and AcAc at pH 9.0 are increased almost 100 fold (relative to those at pH 7.4) and, as would be expected, parallel increases in sulfhydryl protection were observed; i.e., DEM slowed acrolein-induced thiol loss from −78.7±6.2 nmol s$^{-1}$ to −59.7±5.1 nmol s$^{-1}$ and AcAc slowed the rate of loss from −24.9±3.6 nmol s$^{-1}$ to −2.43±2.2 nmol s$^{-1}$. TFPD (pKa=4.2) is completely ionized (>99%) at pH 7.4 and an increase in pH will not significantly alter the corresponding enolate concentration. Hence, no increase in sulfhydryl protection was expected for TFPD and none was observed at the higher pH.

Example III

In Vitro Studies with 2-Acetylcyclopentanone (2-ACP)

This study was carried out in accordance with the NIH Guide for Care and Use of Laboratory Animals and approved by the Montefiore Medical Center Animal Care and Use Committee. Adult male rats (Sprague-Dawley, Taconic Farms, Germantown, N.Y., USA) were used in this study. Rats were housed individually in polycarbonate boxes, and drinking water and Purina Rodent Laboratory Chow (Purina Mills, Inc., St. Louis, Mo., USA) were available ad libitum.

2-ACP Toxicity in Rats and Protection from Hepatotoxicity Induced by Carbon Tetrachloride:

Male rats (200-250 gm) were injected (i.p.) with 2-ACP at three different daily dose-rates: 100, 200 or 300 mg/kg/d×14 days. Rats were observed 3 times per week for signs of developing toxicity; i.e., body weight loss, general appearance, water/food consumption, gait performance and home cage behavior. Regardless of dose-rate, 2-ACP did not cause overt signs of toxicity. As a model of in vivo oxidative stress, rats (200-250 gm) were administered 30 µl of carbon tetrachloride (CCl$_4$) in corn oil (ip) following six daily doses of 2-ACP (200 mg/kg/d) by gavage. Twenty-four hours after CCl$_4$ intoxication, plasma biomarkers of hepatotoxicity, alanine transferase (ALT) and aspartate transferase (AST) were determined Results indicate that 2-ACP pretreatment of CCl$_4$-intoxicated rats significantly reduced the appearance of ALT by 40% and AST by 52% in plasma relative to rats treated with toxicant only. These findings indicate that 2-ACP decreased the degree of hepatic cell death caused by CCl$_4$.

REFERENCES

1. Arancibia, V., Valderrama, M., Silva, K. and Tapia, T. (2003) Determination of chromium in urine samples by complexation-supercritical fluid extraction and liquid or gas chromatography. *J. Chromatog.* 785, 303-309.
2. Awasthi, S., Srivatava, S. K., Piper, J. T., Singhal, S. S., Chaubey, M. and Awasthi, Y. (1996) Curcumin protects against 4-hydroxy-2-nonenal-induced cataract formation in rat lenses. *Am. J. Clin. Nutr.* 64, 761-766.
3. Aggarwal, B. B., Sundaram, C., Malani, N. and Ichikawa, H. (2007) Curcumin: the Indian solid gold. *Adv. Exp. Med. Biol.* 595, 1-75.
4. Ak, T. and Gulcin, I. (2008) Antioxidant and radical scavenging properties of curcumin. *Chem.-Biol. Inter.* 174, 27-37.
5. Anderson, M. M., Hazen, S. L., Hsu, F. F. and Heinecke, J. W. (1997) Human neutrophils employ the myeloperoxidase-hydrogen peroxide-chloride system to convert hydroxy-amino acids into glycolaldehyde, 2-hydroxypropanal and acrolein. *J. Clin. Invest.* 99: 424-432.
6. Arts, I. C. W. and Hollman, P. C. H. (2005) Polyphenols and disease risk in epidemeologic studies. *Am J. Clin. Nutr.* 81, 317S-325S.
7. Banerjee, A., Kunwar, A., Mishra, B. and Priyadarsini, K. I. (2008) Concentration dependent antioxidant/pro-oxidant activity of curcumin studies from AAPH induced hemolysis of RBCs. *Chem.-Biol. Inter.* 174, 134-139.
8. Barber, D. S. and LoPachin, R. M. (2004). Proteomic analysis of acrylamide-protein adduct formation in rat brain synaptosomes. *Toxicol. Appl. Pharmacol.* 201, 120-136.
9. Barber, D. S., Stevens, S, and LoPachin, R. M. (2007) Proteomic analysis of rat striatal synaptosomes during acrylamide intoxication at a low dose-rate. *Toxicol. Sci.* 100, 156-167.
10. Barik, A., Mishra, B., Kunwar, A., Kadam, R. M., Shen, L., Dutta, S., Padhye, S., Satpati, A. K., Zhang, H. and Priyadarsini, K. I. (2007) Comparative study of copper(II)-curcumin complexes as superoxide dismutase mimics and free radical scavengers. *Europ. J. Med. Chem.* 42, 431-439.
11. Balasubramanian, K. (2006) Molecular orbital basis for yellow curry spice curcumin's prevention of Alzheimer' disease. *J. Agric. Food Chem.* 54, 3512-3520.
12. Begum, A. N., Jones, M. R., Lim, G. P., Morihara, T., Kim, P., Heath, D. D., Rock, C. L., et al. (2008) Curcumin structure-function, bioavailability and efficacy in models of neuroinflammation and Alzheimer's disease. *J. Pharmacol. Exp. Ther.* 326, 196-208.
13. Beretta, G., Furlanetto, S., Regazzoni, L., Zarrella, M. and Facino, R. M. (2008) Quenching of α,β-unsaturated aldehydes by green tea polyphenols: HPLC-ESI-MS/MS studies. *J. Pharmact. Biomed. Analy.* 48, 606-611.
14. Bisesi, M. S. (1994) Esters. 3. Esters of alkenylcarboxylic acids and mono-alcohols. In *Patty's Inducstrial Hygiene and Toxicology*, 4$^{th}$ ed. (G. D. Clayton and F. E. Clayton, Eds.) Vol 11, pp. 2999-3007. John Wiley and Sons, NY.
15. Bravo, L. (1998) Polyphenols: chemistry, dietary sources, metabolism and nutritional significance. *Nutr. Rev.* 56, 317-333.

16. Bug, T. and Mayr, H. (2003) Nucleophilic reactivities of carbanions in water: the unique behavior of the malodinitrile anion. *J. Am. Chem. Soc.* 125, 12980-12986.
17. Cai, J., Bhatnagar, A. and Pierce, W. M. (2009). Protein modification by acrolein: formation and stability of cysteine adducts. *Chem. Res. Toxicol.* 22, 708-716.
18. Calabrese, V., Cornelius, C., Mancuso, C., Pennisi, G., Calafato, S., Bellia, F., Bates, T. E., Stella, A. M., Schapira, T., Dinkova-Kostova, A. T. and Rizzarelli, E. (2008) Cellular stress response: a novel target for chemoprevention and nutritional neuroprotection in aging, neurodegernative disorders and longevity. *Neurochem. Res.* 33, 2444-2471.
19. Cho, J., Kim, S., Lee, S., Park, J. A., Kim, S, and Chun, H. S. (2008) Protective effect of the green tea component, theanine on environmental toxins-induced neuronal cell death. *NeuroToxicology* 29, 656-662.
20. Choi, H. K., Won, L., Roback, J. D., Wainer, B. H. and Heller, A. (1992) Specific modulation of dopamine expression in neuronal hybrid cells by primary cells from different brain regions. *Proc. Natl. Acad. Sci.* 89, 8943-8947.
21. Coles, B. (1984-85) Effects of modifying structure on electrophilic reactions with biological nucleophiles. *Drug Met. Rev.* 15, 1307-1334.
22. Dalle-Donne, I., Vistoli, G., Gamberoni, L., Giustarini, D., Colmbo, R., Facino, R. M., Rossi, R., Milzani, A. and Aldini, G. (2007). Actin Cys374 as a nucleophilic target of α,β-unsaturated aldehydes. *Free Rad. Biol. Med.* 42, 583-598.
23. Ding, R., Katebzadeh, K., Roman, L., Bergquist, K. and Lindstrom, U. M. (2006) Expanding the scope of Lewis acid catalysis in water: remarkable ligand acceleration in aqueous ytterbium triflate catalyzed Michael addition reactions. *J. Org. Chem.* 71, 352-5.
24. Dinkova-Kostova, A. T., Talalay, P. (1999). Relation of structure of curcumin analogs to their potencies as inducers of Phase 2 detoxification enzymes. *Carcinogenesis* 20, 911-4.
25. Dinkova-Kostova, A. T., Massiah, M. A., Bozak, R. E., Hicks, R. J. and Talalay, P. (2001). Potency of Michael reaction acceptors as inducers of enzymes that protect against carcinogenesis depends on their reactivity with sulfhydryl groups. *Proc. Natl. Acad. Sci.* 98, 3404-3409.
26. Ehrnhoefer, D. E., Duennwald, M., Markovic, P., Wacker, J. L., Engemann, S., Roark, M., Legleiter, J., Marsh, J. L., Thompson, L. M., Lindquist, S., Muchowski, P. J. and Wanker, E. E. (2006) Green tea-epigallocatechin-gallate modulates early events in Huntington misfolding and reduces toxicity in Huntington's disease models. *Human Mol. Gen.* 15, 2743-2751.
27. Ellis, E. M. (2007) Reactive carbonyls and oxidative stress: potential for therapeutic intervention. *Pharmacol Ther.* 115, 13-24.
28. Esterbauer, H., Schaur, R. J. and Zollner, J. (1991). Chemistry and biochemistry of 4-hydroxynonenal, malonaldehyde and related aldehydes. *Free Rad. Biol. Med.* 11: 81-128.
29. Fujishita, K., Ozawa, T., Shibata, K., Tanabe, S., Sato, Y., Hisamoto, M., Okuda, T. and Koizumi, S. (2009) Grape seed extract acting on astrocytes reveals neuronal protection against oxidative stress via interleukin-6-mediated mechanisms. *Cell Mol. Neurobiol.* DOI 10.1007/s10571-009-9403-5
30. Fu, W., Luo, H., Parthasarathy, S, and Mattson, M. P. (1998) Catecholamines potentiate amyloid peptide neurotoxicity: involvement of oxidative stress, mitochondrial dysfunction and perturbed calcium homeostatsis. *Neurobiol. Dis.* 5, 229-243.
31. Galati, G., Sabzevari, O., Wilson, J. X. and O'Brien, P. J. (2002) Prooxidant activity and cellular effects of the phenoxyl radicals of dietary flavonoids and other polyphenolics. *Toxicology* 177, 91-104.
32. Galati, G. and O'Brien, P. J. (2004) Potential toxicity of flavonoids and other dietary phenolics: significance for their chemopreventive and anticancer properties. *Free Rad. Biol. Med.* 37, 287-303.
33. Halliwell, B. (2006). Oxidative stress and neurodegeneration: where are we now? *J. Neurochem.* 97, 1634-1658.
34. Hara, T., Kanai, S., Mori, K., Mizugaki, T., Ebitani, K., Jitsukawa, K. and Kaneda, K. (2006) Highly efficient C—C bond-forming reactions in aqueous media catalyzed by monomeric vanadate species in an apatite Framework. *J. Org. Chem.* 71, 7455-7462.
35. Hatcher, H., Planalp, R., cho, J., Torti, F. M. and Torti, S. V. (2008) Curcumin: from ancient medicine to current clinical trials. *Cell. Mol. Life. Sci.* 65, 1631-1652.
36. Hertel, C., Terzi, E., Hauser, N., Jakob-Rotne, R., Seelig, J. and Kemp, J. A. (1997) Inhibition of the electrostatic interaction between amyloid peptide and membranes prevents amyloid-induced toxicity. *Proc. Natl. Acad. Sci.* 94, 9412-9416.
37. Hinson, J. A. (1992) Role of covalent and noncovalent interactions in cell toxicity: effects on proteins. *Ann. Rev. Pharmacol. Toxicol.* 32, 471-510.
38. Hsu, C. and Cheng, A. (2007) Clinical studies with curcumin. *Adv. Exp. Med. Biol.* 595, 471-480.
39. Hwang, J. J., Lee, S., Kim, T., Cho, J., K. and Koh, J. (2008) Zinc and 4-hydroxy-2-nonenal mediate lysosomal membrane permeabilization induced by $H_2O_2$ in cultured hippocampal neurons. *J. Neurosci.* 28, 3114-3122.
40. Iqbal, M., Okazaki, Y. and Okada, S. (2009) Curcumin attenuates oxidative damage in animals treated with a renal carcinogen, ferric nitrilotriacetate (Fe-NTA): implications for cancer prevention. *Mol. Cell. Biochem.* 324, 157-164.
41. Jaramillo, P., Periz, P., Contreas, R., Tiznada, W. and Fuentealba, P. (2006) Definition of a nucleophilicity scale. *J. Phys. Chem.* 110, 8181-8187.
42. Jenner, P. (2003). Oxidative stress in Parkinson's disease. *Ann. Neurol.* 53, S26-S38.
43. Jiao, Y., Wilkinson, J., Pietsch, E. C., Buss, J. L., Wang, W., Planalp, R., Torti, F. M. and Torti, S. V. (2006) Iron chelation in the biological activity of curcumin. *Free Rad. Biol. Med.* 40, 1152-1160
44. Kampa, M., Nifli, A. P., Notas, G. and Costanas, E. (2007) Polyphenols and cancer cell growth. *Rev. Physiol. Biochem. Pharmacol.* 159, 79-113.
45. Kehrer, J. P., Biswal, S. S. (2000) The molecular effects of acrolein. *Toxicol Sci.* 57, 6-15.
46. Kurien, B. T. and Scofield, R. H. (2007) Curcumin/turmeric solubilized in sodium hydroxide inhibits HNE protein modification—An in vitro study. *J. Ethnopharmacol.* 110, 368-373.
47. Lavoie, S., Chen, Y., Dalton, T. P., Gysin, R., Cuenod, Mi., Steullet, P. and Do, K. Q. (2009) Curcumin, quercetin, and tBHQ modulate glutathione levels in astroctyes and neurons: importance of the glutamate cysteine ligase modifier subunit. *J. Neurochem.* 108, 1410-1422.
48. Lee, D. W. and Opanashuk, L. A. (2004) Polychlorinated biphenyl mixture aroclor 1254-induced oxidative stress plays a role in dopaminergic cell injury. *Neurotoxicology* 25, 925-939.
49. Lin, M. T. and Beal, M. F. (2006) Mitochondrial dysfunction and oxidative stress in neurodegenerative diseases. *Nature* 443, 787-795.

50. Litwinienko, G. and Ingold, K. U. (2004) Abnormal solvent effects on hydrogen atom abstraction. 2. Resolution of the curcumin antioxidant controversy. The role of sequential proton loss electron transfer. *J. Org. Chem.* 69, 5888-5896.
51. Lo, C., Li, S D., Tan, D., Pan, M., Sang, S, and Ho, C. (2006) Trappings reactions of reactive carbonyl species with tea polyphenols in simulated physiological conditions. *Mol. Nutr. Food Res.* 50, 1118-1128.
52. LoPachin, R. M., Schwarcz, A. I., Gaughan, C. L., Mansukhani, S, and Das, S. (2004). In vivo and in vitro effects of acrylamide on synaptosomal neurotransmitter uptake and release. *NeuroToxicology* 25, 349-363.
53. LoPachin, R. M. and DeCaprio, A. P. (2005) Protein adduct formation as a molecular mechanism of neurotoxicity. *Toxicol. Sci.* 86, 214-225.
54. LoPachin, R. M. Barber, D. S., He, D. and Das, S. (2006). Acrylamide inhibits dopamine uptake in rat striatal synaptic vesicles. *Tox Sci.* 89, 224-234.
55. LoPachin, R. M. and Barber, D. S. (2006). Synaptic cysteine sulfhydryl groups as targets of electrophilic neurotoxicants. *Tox. Sci.* 94, 240-255.
56. LoPachin, R. M., Barber, D. S., Geohagen, B. C., Gavin, T., He, D. and Das, S. (2007). Structure-toxicity analysis of Type-2 alkenes: in vitro neurotoxicity. *Tox. Sci.* 95: 136-146.
57. LoPachin, R. M., Gavin, T., Geohagen, B. C. and Das, S. (2007). Neurotoxic mechanisms of electrophilic type-2 alkenes: soft-soft interactions described by quantum mechanical parameters. *Tox. Sci.* 98: 561-570.
58. LoPachin, R. M., Barber, D. S. and Gavin, T. (2008). Molecular mechanisms of the conjugated $\alpha,\beta$-unsaturated carbonyl derivatives: relevance to neurotoxicity and neurodegenerative diseases. *Tox. Sci.* 104, 235-249.
59. LoPachin, R. M., Gavin, T. and Barber, D. S. (2008). Type-2 alkenes mediate synaptotoxicity in neurodegenerative diseases. *NeuroToxicology* 29, 871-882.
60. LoPachin, R. M. and Gavin, T. (2008). Acrylamide-induced nerve terminal damage: relevance to neurotoxic and neurodegenerative mechanisms. *J. Agric. Food Chem.* 56, 5994-6003.
61. LoPachin, R. M., Gavin, T., Geohagen, B. C. and Das, S. (2009). Synaptosomal toxicity and nucleophilic targets of 4-hydroxy-2-nonenal. *Tox. Sci.* 107: 171-181.
62. LoPachin, R. M., Gavin, T., Petersen, D. R. and Barber, D. S. (2009). Molecular mechanisms of 4-hydroxy-2-nonenal and acrolein toxicity: nucleophilic targets and adduct formation. *Chem. Res. Toxicol.* 22: 1499-1508.
63. Loudon, G. M. (2002) *Organic Chemistry* ($4^{th}$ ed.) Oxford University Press, NY; Chapt. 22; pg. 997.
64. Mandel, S, and Youdim, M. B. H. (2004) Catechin polyphenols: neurodegeneration and neuroprotection in neurodegenerative diseases. *Free Rad. Biol. Med.* 37, 304-317.
65. Mandel, S., Amit, T., Bar-Am, O and Youdim, M. B. H. (2007) Iron dysregulation in Alzheimer's disease: multimodal brain permeableiron chelating drugs, possessing neuroprotective-neurorescue and amyloid precursor protein-processing regulatory activities as therapeutic agents. *Prog. Neurobiol.* 82, 348-360.
66. Martell, A. E. and Smith, R. M. (1977) *Critical Stability Constants*. New York, Plenum Press; pg. 654-676.
67. Mattson, M. P. and Cheng, A. (2006) Neurohormetic phytochemicals: low-dose toxins that induce adaptive neuronal stress responses. *Trends Neurosci.* 29, 632-639.
68. Maynard, A. T., Huang, M., Rice, W. G. and Covell, D. G. (1998). Reactivity of the HIV-1 nucleocapsid protein p7 zinc finger domains from the perspective of density-functional theory. *Proc. Natl. Acad. Sci.* 95: 11578-11583.
69. Miyake, T. and Shibamoto, T. (1996) Simultaneous determination of acrolein, malonaldehyde and 4-hydroxy-2-nonenal produced from lipids oxidized with Fenton's reagent. *Food Chem. Toxicol.* 34, 1009-1011.
70. Morel, I., Lescoat, G., Cogrel, P., Serent, O., Pasdeloup, N., Brissot, P., Cillard, P. and Cillard, J. (1993) Antioxidant and iron-chelating activities of the flavonoids catechin, quercetin and diosmetin on iron-loaded rat hepatocyte cultures. *Biochem. Pharmacol.* 45, 13-19.
71. Nakagawa, H., Hasumi, K., Woo, J., Nagai, K. and Wachi, M. (2004) Generation of hydrogen peroxide primarily contributes to the induction of Fe(II)-dependent apoptosis in Jurkat cells by epigallocatechin gallate. *Carcnogenisis* 25, 1567-1574.
72. Negre-Slavayre, A., Coatrieux, C., Ingueneau, C. and Salvayre, R. (2008) Advanced lipid peroxidation end products in oxidative damage to proteins. Potential role in diseases and therapeutic prospects for the inhibitors. *Brit. J. Pharmacol.* 153, 6-20.
73. Nelson, S. D. and Pearson, P. G. (1990) Covalent and noncovalent interactions in acute lethal cell injury caused by chemicals. *Ann. Rev. Pharmacol. Toxicol.* 30, 169-195.
74. Pandey, N., Strider, J., Nolan, W. C., Yan, S. X and Galvin, J. E. (2008) Curcumin inhibits aggregation of $\alpha$-synuclein. *Acta Neuropath.* 115, 479-489.
75. Payton, F., Sandusky, P. and Alworth, W. L. (2007) NMR study of the solution structure of curcumin. *J. Nat. Prod.* 70, 143-146.
76. Pearson, R. G. (1990). Hard and soft acids and bases—the evolution of a chemical concept. *Coord. Chem. Rev.* 100, 403-425.
77. Petersen, D. R., and Doom, J. A. (2004). Reactions of 4-hydroxynonenal with proteins and cellular targets. *Free Rad. Biol. Med.* 37, 937-945.
78. Raza, H., Hohn, A, Brown, E. M., Benedict, S, and Kambal, A. (2008) Alterations in mitochondrial respiratory functions, redox metabolism and apoptosis by oxidant 4-hydroxynonenal and antioxidants curcumin and melatonin in PC12 cells. *Toxicol. Appl. Pharmacol.* 226, 161-168.
79. Satoh, T. and Lipton, S. A. (2006) Redox regulation of neuronal survival mediated by electrophilic compounds. *Trends Neurosci.* 30, 37-45.
80. Sang, S., Shao, X., Bai, N., Lo, C., Yang, C. S. and Ho, C. (2007) Tea polyphenol (−) Epigallocatechin-3-gallate: a new trapping agent of reactive dicarbonyl species. *Chem. Res. Toxicol.* 20, 1862-1870
81. Sayre, L. M., Perry, G. and Smith, M. A. (2008) Oxidative stress and neurotoxicity. *Chem. Res. Toxicol.* 21, 173-188.
82. Scapagnini, G., Foresti, R., Calabrese, V., Stella, A. M. G., Green, C. J. and Motterlini, R. (2002) Caffeic acid phenethyl ester and curcumin: a novel class of heme oxygenase-1 inducers. *Mol. Pharmacol.* 3: 554-561.
83. Schultz, T. W., Netzeva, T. I., Roberts, D. W. and Cronin, M. T. D. (2005) Structure-toxicity relationships for the effects to *Tetrahymena pyriformis* of aliphateic carbonyl-containing $\alpha,\beta$-unsaturated chemicals. *Chem. Res. Toxicol.* 18, 330-341.
84. Schultz, T. W., Carlson, R. E., Cronin, M. T. D., Hermens, J. L. M., Johnson, R., O'Brien, P. J., Roberts, D. W., Siraki, A., Wallace, K. B. and Veith, G. D. (2006). A conceptual framework for predicting the toxicity of reactive chemicals: modeling soft electrophilicity. *SAR QSAR Eviron. Res.* 17, 413-428.

85. Shao, X., Bai, N., He, K., Ho, C., Yang, C. S. and Sang, S. (2008) Apple polyphenols, phloretin and phloridzin: new trapping agents of reactive dicarbonyl species. *Chem. Res. Toxicol.* 21, 2042-2050.

86. Smith, M. B. and March, J. (2001) *Advanced Organic Chemistry* (5$^{th}$ ed.) John Wiley and Sons, NY; Chapt. 15; pg. 1022.

87. Strasser, E. M., Wessner, B., Manhart, N. and Roth, E. (2005) The relationship between the anti-inflammatory effects of curcumin and cellular glutathione content in myelomonocytic cells. *Biochem. Pharmacol.* 70, 552-559.

88. Shen, L., Zhang, H. and Ji, H. (2005) A theoretical study on Cu(II)-chelating properties of curcumin and its implications for curcumin as a multipotent agent to combat Alzheimer's disease. *J. Mol. Struct.* 757, 199-202.

89. Vajragupta, O., Boonchoong, P., Morris, G. M. and Olson, A. J. (2005) Active site binding modes of curcumin in HIV-1 protease and integrase. *Bioorg. Med. Chem. Lett.* 15, 3364-3368.

90. Van Iersel, M. L. P. S., Ploemen, J-P. H. T. M., LoBello, M., Federici, G. and van Bladeren, P. J. (1997). Interactions of α,β-unsaturated aldehydes and ketones with human glutathione S-transferase P1-1. *Chem-Biol. Inter.* 108, 67-78.

91. Villamena, F. A., Merle, J. K., Hadad, C. M. and Zweier, J. L. (2005) Superoxide radical anion adduct of 5,5-dimethyl-1-pyrroline N-oxide (DMPO). 1. The thermodynamics of formation and its acidity. *J. Phys. Chem. A.* 109, 6083-6088.

92. Wang, Y., Pan, M., Cheng, A., Lin, L., Ho, Y., Hsieh, C. and Lin, J. (1997) Stability of curcumin in buffer solutions and characterization of its degradation products. *J. Pharmaceut. Biomed. Analy.* 15, 18667-1876.

93. Weber, W. M., Hunsaker, L. A., Gonzales, A. M., Heynekamp, J. J., Orlando, R. A., Deck, L. M. and Vander Jagt, D. L. (2006) TPA-induced up-regulation of activator protein-1 can be inhibited or enhanced by analogs of the natural product curcumin. *Biochem. Pharmacol.* 72, 928-940.

94. Witz, G. (1989). Biological interactions of α,β-unsaturated aldehydes. *Free Rad. Biol. Med.* 7, 333-349.

95. Wood, P. L., Khan, M. A., Kulow, S. R., Mahmood, S. A. and Moskal, J. R. (2006) Neurotoxicity of reactive aldehydes: the concept of "aldehyde load" as demonstrated by neuroprotection with hydroxylamines *Brain Res.* 1095: 190-199.

96. Wood, P. L., Khan, M. A., Moskal, J. R., Todd, K. G., Tanay, V. M. and Baker, G. (2006) Aldehyde load in ischemia-reperfusion brain injury: neuroprotection by neutralization of reactive aldehydes with phenelzine. *Brain Res.* 1122: 184-190.

97. Wood, P. L., Khan, M. A. and Moskal, J. R. (2007) The concept of "aldehyde load" in neurodegenerative mechanisms: cytotoxicity of the polyamine degradation products hydrogen peroxide, acrolein, 3-aminopropanal, 3-acetamidopropanal and 4-aminobutanal in a retinal ganglion cell line. *Brain Res.* 1145: 150-156.

98. Yoshino, M., Haneda, M., Naruse, M., Htay, H. H., Tsubouchi, R., Qiao, S. L., Li, W. H., Murakami, K. and Yokochi, T. (2004) Prooxidant activity of curcuim: copper-dependent formation of 8-hydroxy-2'-deoxyguanosine in DNA and induction of apoptotic cell death. *Toxicol. In vitro* 18, 783-789.

99. Youdim, K. A. and Joseph, J. A. (2001) A possible emerging role of phytochemicals in improving age-related neurological dysfunctions: a multiplicty of effects. *Free Rad. Biol. Med.* 30, 583-594.

100. Yuting, C., Rongliang, Z., Zhongijan, J and Young, J. (1990) Flavonoids as superoxide scavengers and antioxidants. *Free Rad. Biol. Med.* 9, 19-21.

101. Zhu, Q., Liang, C., Cheng, M K., Peng, X., Lo, C. L., Shahidi, F., Chen, F., Ho, C. and Wang, M. (2009) Trapping effects of green and black tea extracts on peroxidation-derived carbonyl substances of seal blubber oil. *J. Agric. Food Chem.* 57, 1065-1069.

102. Zhu, Q., Zheng, Z., Cheng, M K., Wu, J., Zhang, S., Tang, Y. S., Sze, K., Chen, J., Chen, F. and Wang, M. (2009) Natural polyphenols as direct trapping agents of lipid peroxidation-derived acrolein and 4-hydroxy-2-nonenal. *Chem. Res. Toxicol.* DOI 10.1021/tx900221s.

103. LoPachin R M, Gavin T, Geohagen B C, Zhang L, Casper D, Lekhraj R, Barber D S. β-Dicarbonyl enolates: a new class of neuroprotectants. *J. Neurochem.* 2011 January; 116(1):132-43. Epub 2010 Dec. 2.

104. Dairam A., Fogel R., Daya S, and Limson J. L. (2008) Antioxidant and iron-binding properties of curcumin, capsaicin and S-allylcysteine reduce oxidative stress in rat brain homogenate. *J. Agric. Food. Chem.* 56, 3350-3356.

What is claimed is:

1. A method of treating a subject with a disease or tissue injury mediated by cellular oxidative stress, wherein the disease or tissue injury is atherosclerosis, diabetes, Alzheimer's disease, stroke or traumatic spinal cord injury, the method comprising administering to the subject a therapeutically effective amount of a compound of formula (I)

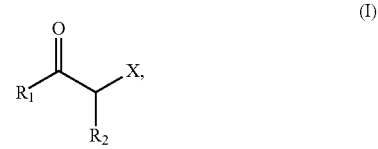

wherein $R_1$ and $R_2$ are independently H, alkyl, alkoxy alkyl, acyloxy alkyl, aryl, aryloxy, acyloxy aryl, heteroaryl, heteroaryloxy, or acyloxy heteroaryl;

X is $COR_3$, $CO_2R_3$, $NO_2$, CN, $CON(R_3)_2$, or $SO_2R_3$;

$R_3$ is H, alkyl, alkoxy alkyl, acyloxy alkyl, aryl, aryloxy, acyloxy aryl, heteroaryl, heteroaryloxy, acyloxy heteroaryl, or trifluoromethyl; and/or $R_2$ forms a ring together with either $R_1$ or $R_3$, or $R_2$ forms rings with both $R_1$ and $R_3$;

wherein any ring formed between $R_2$ with $R_1$ and/or $R_3$ optionally and independently contains one or more O, S, N or substituted N, where substitution at N is an alkyl or acyl group;

wherein any alkyl can independently be branched or unbranched;

wherein any aryl or heteroaryl can independently be optionally substituted with —CH3, —NH2, —OH, =O, halogen, alkyl, alkoxy, acyloxy, aryl and/or acyloxyaryl;

or a tautomer thereof; or a geometric or optical isomer thereof; or racemate thereof;

or a pharmaceutically acceptable salt thereof.

2. The method of claim 1, wherein the compound has the structure

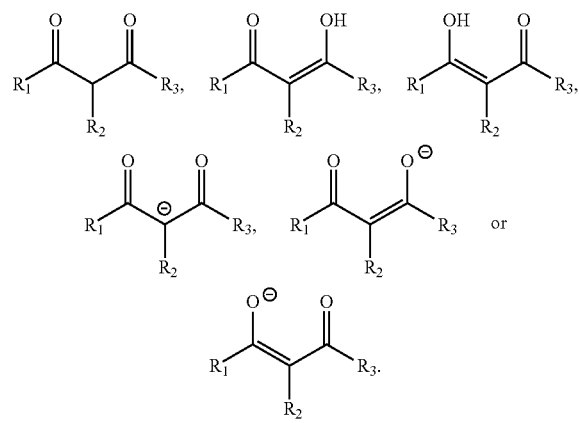

3. The method of claim 1, wherein any ring formed between $R_2$ with $R_1$ and/or $R_3$ is independently a 4-12 member ring.

4. The method of claim 3, wherein any ring formed between $R_2$ with $R_1$ and/or $R_3$ is independently a 5-6 member ring.

5. The method of claim 1, wherein any ring formed between $R_2$ with $R_1$ and/or $R_3$ independently contains one or more O, S, N or substituted N, where substitution at N is an alkyl or acyl group.

6. The method of claim 1, wherein any alkyl is independently C1-C6 alkyl.

7. The method of claim 6, wherein any alkyl is independently C1-C3 alkyl.

8. The method of claim 1, wherein the compound has the structure

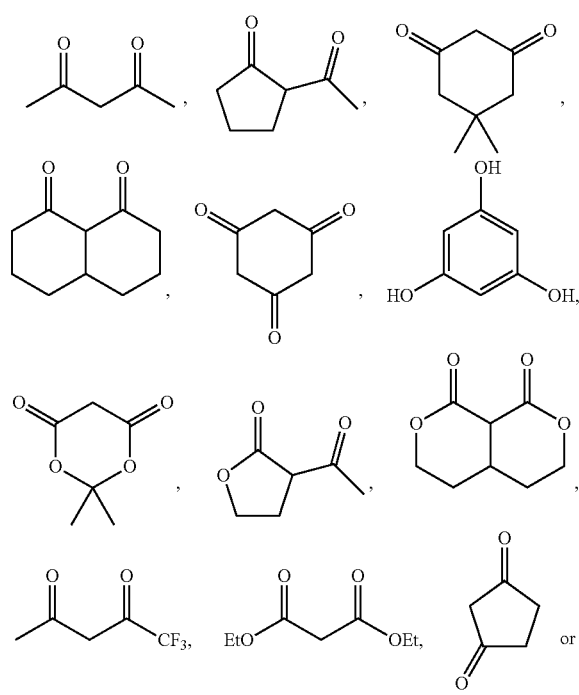

-continued

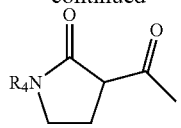

wherein $R_4$=H, alkyl, alkoxy, acyloxy, aryl or acyloxyaryl; or a tautomer thereof.

9. The method of claim 1, wherein the compound has the structure

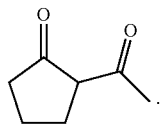

10. The method of claim 1, wherein the compound reduces hepatotoxicity.

11. A method of providing a nutritional supplement to a subject comprising administering to the subject a compound of formula (I)

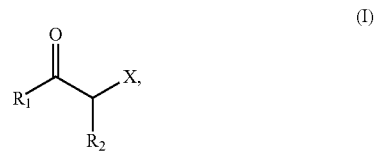

wherein
  $R_1$ and $R_2$ are independently H, alkyl, alkoxy alkyl, acyloxy alkyl, aryl, aryloxy, acyloxy aryl, heteroaryl, heteroaryloxy, or acyloxy heteroaryl;
  X is $COR_3$, $CO_2R_3$, $NO_2$, CN, $CON(R_3)_2$, or $SO_2R_3$;
  $R_3$ is H, alkyl, alkoxy alkyl, acyloxy alkyl, or trifluoromethyl; and/or
  $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group;
  wherein any alkyl can independently be branched or unbranched;
  wherein any aryl or heteroaryl can independently be optionally substituted with —CH3, —NH2, —OH, =O, halogen, alkyl, alkoxy, acyloxy, aryl and/or acyloxyaryl;
  or a tautomer thereof; or a geometric or optical isomer thereof; or racemate thereof;
  or a pharmaceutically acceptable salt thereof.

12. The method of claim 11, wherein the compound has the structure

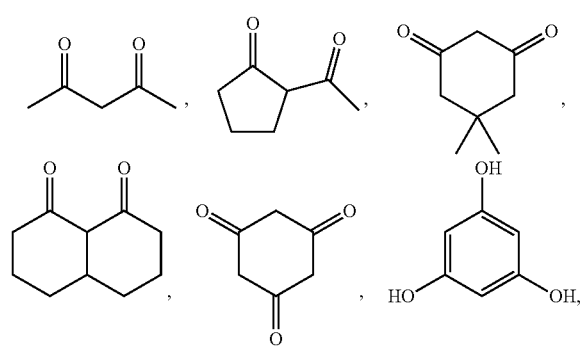

-continued

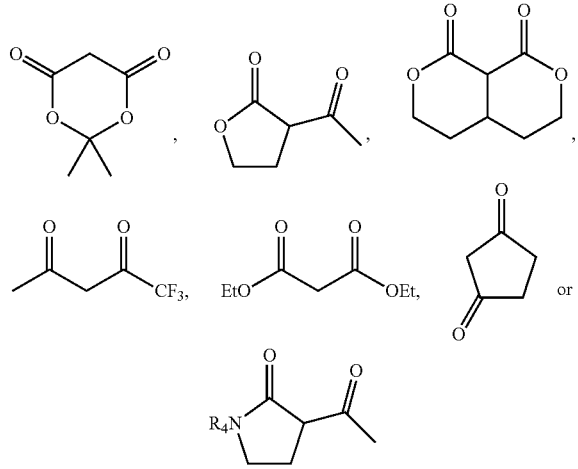

wherein R₄=H, alkyl, alkoxy, acyloxy, aryl or acyloxyaryl; or a tautomer thereof.

13. A method of treating the skin of a subject comprising administering to the skin of the subject a compound of formula (I)

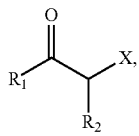

wherein $R_1$ is H, alkyl, alkoxy alkyl, or acyloxy alkyl;

$R_2$ is H, alkyl, alkoxy alkyl, acyloxy alkyl, aryl, aryloxy, acyloxy aryl, heteroaryl, heteroaryloxy, or acyloxy heteroaryl;

X is $COR_3$, $CO_2R_3$, $NO_2$, CN, $CON(R_3)_2$, or $SO_2R_3$;

$R_3$ is H, alkyl, alkoxy alkyl, acyloxy alkyl, or trifluoromethyl; and/or $R_2$ forms a ring together with either $R_1$ or $R_3$, or $R_2$ forms rings with both $R_1$ and $R_3$; wherein any ring formed between $R_2$ with $R_1$ and/or $R_3$ optionally and independently contains one or more O, S, N or substituted N, where substitution at N is an alkyl or acyl group;

wherein any alkyl can independently be branched or unbranched;

wherein any aryl or heteroaryl can independently be optionally substituted with —CH3, —NH2, —OH, =O, halogen, alkyl, alkoxy, acyloxy, aryl and/or acyloxyaryl;

or a tautomer thereof; or a geometric or optical isomer thereof; or racemate thereof;

or a pharmaceutically acceptable salt thereof.

14. The method of claim 13, wherein the compound is used to treat an aging effect on the skin or to treat sun damage to the skin.

15. The method of claim 14, wherein the compound is used to treat wrinkles.

* * * * *

UNITED STATES PATENT AND TRADEMARK OFFICE
CERTIFICATE OF CORRECTION

PATENT NO.         : 8,835,510 B2
APPLICATION NO.    : 13/699314
DATED              : September 16, 2014
INVENTOR(S)        : Richard M. LoPachin and Terrence Gavin It is certified that error appears in the above-identified patent and that said Letters Patent is hereby corrected as shown below:

In the specification,

Column 1, lines 15-21, should read:

-- STATEMENT OF GOVERNMENT SUPPORT

This invention was made with government support under grant number ES003830 awarded by the National Institutes of Health. The government has certain rights in the invention. --

Signed and Sealed this
Third Day of November, 2015

Michelle K. Lee
*Director of the United States Patent and Trademark Office*